United States Patent
Smith et al.

(10) Patent No.: US 8,580,798 B2
(45) Date of Patent: Nov. 12, 2013

(54) SUBSTITUTED PYRIMIDINE DERIVATIVES USEFUL IN THE TREATMENT OF CANCER AND OTHER DISORDERS

(75) Inventors: Roger Smith, Chester Springs, PA (US); Jacques Dumas, Carlisle, MA (US); Gan Wang, Wallingford, CT (US); Wendy Lee, San Ramon, CA (US); Karl Miranda, Lexington, MA (US)

(73) Assignee: Bayer Intellectual Property GmbH, Monheim (DE)

( * ) Notice: Subject to any disclaimer, the term of this patent is extended or adjusted under 35 U.S.C. 154(b) by 571 days.

(21) Appl. No.: 12/158,524

(22) PCT Filed: Dec. 20, 2006

(86) PCT No.: PCT/US2006/048382
§ 371 (c)(1),
(2), (4) Date: Sep. 22, 2009

(87) PCT Pub. No.: WO2007/075650
PCT Pub. Date: Jul. 5, 2007

(65) Prior Publication Data
US 2010/0081812 A1  Apr. 1, 2010

Related U.S. Application Data

(60) Provisional application No. 60/752,200, filed on Dec. 21, 2005.

(51) Int. Cl.
*C07D 401/12* (2006.01)
*A61K 31/506* (2006.01)

(52) U.S. Cl.
USPC .................... 514/256; 544/296; 544/328

(58) Field of Classification Search
USPC .................... 544/296, 328; 514/256
See application file for complete search history.

(56) References Cited

U.S. PATENT DOCUMENTS

| | | |
|---|---|---|
| 2002/0065296 A1 | 5/2002 | Dumas et al. |
| 2002/0165394 A1 | 11/2002 | Dumas et al. |
| 2003/0105091 A1 | 6/2003 | Riedl et al. |
| 2003/0181442 A1 | 9/2003 | Riedl et al. |
| 2003/0207914 A1 | 11/2003 | Dumas et al. |

FOREIGN PATENT DOCUMENTS

| | | |
|---|---|---|
| EP | 1 777 218 A1 | 4/2007 |
| JP | 2003-526613 | 9/2003 |
| JP | 2005-272474 | 10/2005 |
| WO | WO 99/32106 A1 | 7/1999 |
| WO | WO 99/32110 A1 | 7/1999 |
| WO | WO 99/32111 A1 | 7/1999 |
| WO | WO 99/32455 A1 | 7/1999 |
| WO | WO 00/41698 A1 | 7/2000 |
| WO | WO 00/42012 A1 | 7/2000 |
| WO | WO 02/062763 A2 | 8/2002 |
| WO | WO 02/085857 A2 | 10/2002 |
| WO | WO 2004/078128 A2 | 9/2004 |
| WO | WO 2004/078746 A2 | 9/2004 |
| WO | WO 2004/078747 A1 | 9/2004 |
| WO | WO 2005/075425 A2 | 8/2005 |
| WO | WO 2006/071940 | * 7/2006 |

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition and Expanded, pp. 451 and 596.*
Silverman, Prodrugs and Drug Delivery Systems, The Organic Chemistry of Drug Design and Drug Action, pp. 352-399, 1992.*
Aiello, L. P. et al., "Vascular endothelial growth factor in ocular fluid of patients with diabetic retinopathy and other retinal disorders," The New England Journal of Medicine, Dec. 1, 1994, vol. 331, pp. 1480-1487.
Antoniades, H. N. et al., "Malignant epithelial cells in primary human lung carcinomas coexpress in vivo platelet-derived growth factor (PDGF) and PDGF receptor mRNAs and their protein products," Proc. Natl. Acad. Sci., May 1992, vol. 89, pp. 3942-3946.
Baker, E. A. et al., "Proteinases, their inhibitors, and cytokine profiles in acute wound fluid," Wound Rep Reg, 2000, vol. 8, pp. 392-398.
Bhardwaj, B. et al., "Localization of Platelet-derived growth factor β receptor expression in the Periepithelial Stroma of Human Breast Carcinoma," Clinical Cancer Research, Apr. 1996, vol. 2, pp. 773-782.
Blaschke, F. et al., "Hypoxia activates β-one-integrin via ERK ½and p38 MAP kinase in human vascular smooth muscle cells," Biochemical and Biophysical Research Communications, 2002, vol. 296, pp. 890-896.
Bos, J. L. et al., "ras Oncogenes in Human Cancer: A Review," Cancer Research, Sep. 1, 1989, vol. 49, pp. 4682-4689.
Brown, L. F. et al., "Increased expression of Vascular Permeability Factor (Vascular Endothelial Growth Factor) in Bullous Pemphigold, Dermatitis Herpetiformis, and Erythema Multiforme," J. Invest Dermatol., 1995, vol. 104, pp. 744-749.

(Continued)

*Primary Examiner* — Deepak Rao
(74) *Attorney, Agent, or Firm* — Millen, White, Zelano & Branigan, P.C.

(57) ABSTRACT

Substituted pyrimidine derivatives of formula (I), salts, metabolites, prodrugs and diastereoisomeric forms (both isolated stereoisomers and mixtures of stereoisomers) thereof (wherein A=pyrimidine) pharmaceutical compositions containing such compounds and the use of those compounds or compositions for treating hyper-proliferative and angiogenesis disorders, as a sole agent or in combination with other active ingredients, e.g., cytotoxic therapies.

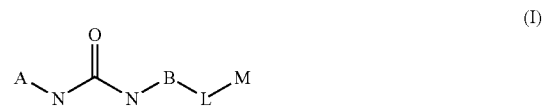

(I)

21 Claims, No Drawings

(56) References Cited

OTHER PUBLICATIONS

Daum, G. et al., "The ins and outs of Raf Kinases," TIBS, Nov. 1994, vol. 19, pp. 474-480.
Ferrara, N. et al., "Molecular and Biological Properties of the Vascular Endothelial Growth Factor Family of Proteins," Endocrine Reviews, 1992, vol. 13, pp. 18-32.
Fleming, T. P. et al., "Amplification and/or over expression of Platelet-derived growth factor receptors and epidermal growth factor receptor in human glial tumors," Cancer Research, Aug. 15, 1992, vol. 52, pp. 450-4553.
Folkman, Judah, "Role of Angiogenesis in Tumor Growth and Metastasis," Seminars in Oncology, 2002, vol. 29, No. 6, Suppl. 16, pp. 15-18.
Forsberg, K. et al., "Platelet-derived growth factor (PDGF) in oncogenesis: Development of a vascular connective tissue stroma in xenotransplanted human melanoma producing PDGF-BB," Proc. Natl. Acad. Sci., Jan. 1993, vol. 90, pp. 393-397.
Fridman, M. et al., "The Minimal Fragments of c-Raf-1 and NF1 That Can Suppress v-Ha-Ras-Induced Malignant Phenotype," The Journal of Biological Chemistry, 1994, vol. 269, No. 48, pp. 30105-30108.
Fudge, K, et al., "Immunohistochemisty Analysis of Platelet-derived Growth Factor A and B Chains and Platelet-derived Growth Factor α and β receptor Expression in Benign Prostatic Hyperplasias and Gleason-graded Human Prostate Adenocarcinomas," Modern Pathology, 1994, vol. 7, No. 5, pp. 549-554.
Funa, K. et al., "Expression of Platelet-derived Growth Factor β-Receptors on Stromal Tissue Cells in Human Carcinoid Tumors," Cancer Research, 1990, vol. 50, pp. 748-753.
George, Daniel, "Platelet-derived Growth Factor Receptors: A Therapeutic Target in Solid Tumors," Semin Oncol, 2001, vol. 28, Suppl. 17, pp. 27-33.
Heinrich, M. C. et al., "PDGFRA Activating Mutations in Gastrointestinal Stromal Tumors," Science, Jan. 2003, vol. 299, pp. 708-710.
Heldin, C. et al., "Binding of Different Dimeric Forms of PDGF to human fibroblasts: evidence for two separate receptor types," The EMBO Journal, 1988, vol. 7, No. 5, pp. 1387-1393.
Heldin, C. et al., "Platelet-derived Growth Factor: Mechanism of Action and Relations to Oncogenes," J. Cell Sci. Suppl., vol. 3, pp. 65-76, (1985).
Heldin, C. et al., "Signal Transduction via platelet-derived growth factor receptors," Biochimica et Biophysica Acta, 1998, pp. F79-F113.
Henriksen, R. et al., "Expression and Prognostic Significance of Platelet-derived Growth Factor and its Receptors in Epithlial Ovarian Neoplasms," Cancer Research, Oct. 1, 1993, vol. 53, pp. 4550-4554.
Huang, S. et al., "Urokinase Plasminogen Activator/Urokinase-specific Surface Receptor Expression and Matrix Invasion by Breast Cancer Cells Requires Constitutive p38α Mitogen-activated Protein Kinase Activity," The Journal of Biological Chemistry, Apr. 21, 2000, vol. 275, No. 16, pp. 12266-12272.
Jiuhong, Yu et al., "Both platelet-derived growth factor receptor (PDGFR)-α and PDGFR-β Promote Murine Fibroblast Cell Migration," Biochemical and Biophysical Research Communication, 2001, vol. 282, pp. 697-700.
Karpanen, T. et al., "Vascular Endothelial Growth Factor C Promotes Tumor Lymphangiogenesis and Intralymphatic Tumor Growth," Cancer Research, Mar. 1, 2001, vol. 16, pp. 1786-1790.
Koch, A. E. et al., "Vascular Endothelial Growth Factor: A Cytokine Modulating Endothelial Function in Rheumatoid Arthritis," Journal of Immunology, 1994, vol. 152, pp. 4149-4156.
Kolch, W. et al., "Raf-1 protein Kinase is required for growth of induced NIH/3T3 cells," Letters to Nature, Jan. 31, 1991, vol. 349, pp. 426-428.
Kourembanas, S. et al., "Mechanisms by which oxygen regulates gene expression and cell-cell interaction in the vasculature," Kidney International, 1997, vol. 51, pp. 483-443.
Kubo, H. et al., "Involvement of vascular endothelial growth factor receptor-3 in maintenance of Integrity of endothelial cell lining during tumor angiogenesis," Blood, Jul. 15, 2000, vol. 96, No. 2, pp. 546-553.

Laferriere, J. et al., "Transendothelial Migration of Colon Carcinoma Cells Requires Expression of E-selection by Endothelial Cells and Activation of Stress-activated Protein Kinase-2 (SAPK2/p38) in the Tumor Cells," The Journal of Biological Chemistry, Sep. 7, 2001, vol. 276, No. 36, pp. 33762-33772.
Lindmark, G. et al., "Stromal Expression of Platelet-derived Growth Factor β-Receptor and Platelet-Derived Growth Factor B-Chain in Colorectal Cancer," Laboratory Investigation, 1993, vol. 69, No. 6, pp. 682-689.
Lopez, P. F. et al., "Transdifferentiated Retinal Pigment Epithelial Cells Are Immunoreactive for Vascular Endothelial Growth Factor in Related Choroidal Neovascular Membranes," Investigate Ophthalmology & Visual Science, Apr. 1996, vol. 37, No. 5.
Lowy, D. R., "Function and Regulation of RAS," Annu. Rev. Biochem, 1993, vol. 62, pp. 851-891.
Makinen, T. et al., " Inhibition of lymphangiogenesis with resulting lymphedema in transgenic mice expressing soluble VEGF receptor-3," Nature Medicine, Feb. 2001, vol. 7, No. 2, pp. 199-205.
Mandriota, S. J. et al., "Vascular endothelial growth factor-C-mediated lymphangiogenesis promotes tumour metastasis," The EMBO Journal, 2001, vol. 20, No. 4, pp. 672-682.
McDonald, N. Q. et al., "A Structural Superfamily of Growth Factors Containing a Cystine Knot Motif," Cell, May 7, 1993, vol. 73, pp. 421-424.
McMahon, Gerald, "VEGF Receptor Signaling in Tumor Angiogenesis," The Oncologist, 2000, vol. 5, suppl. 1, pp. 3-10.
Monia, B. P. et al., "Antitumor activity of a phosphorothioate antisense oligodeoxynucleotide targeted against C-Raf kinase," Nature Medicine, Jun. 1996, vol. 2, No. 6, 668-675.
Mustonen, T. et al., "Endothelial Receptor Tyrosine Kinases Involved in Angiogenesis," The Journal of Cell Biology, May 1995, vol. 129, No. 4, pp. 895-898.
Nakanishi, K. et al., "Expression of Platelet-derived Growth-Factor B-Chain mRNA and Tumor Angiogenesis in Invasive Transitional Cell Carcinoma of the Upper Urinary Tract," Modern Pathology, 1997, vol. 10, No. 4, pp. 341-347.
Naumann, U. et al., "The Role of Raf Kinases in Development and Growth of Tumors," Recent Results in Cancer Research, 1997, vol. 143, pp. 237-244.
Neufeld, G. et al., "Vascular endothelial growth factor (VEGF) and its receptors," FASEB J., 1999, vol. 13, pp. 9-22.
Ostman, A. et al., "Involvement of Platelet-derived Growth Factor in Disease: Development of Specific Antagonists," Advances in Cancer Research, 2001, vol. 80, pp. 1-38.
Peacock, D. J. et al., "Angiogenesis Inhibition Suppresses Collagen Arthritis," J. Exp. Med., Apr. 1992, vol. 175, pp. 1135-1138.
Pe'er, J. et al., "Hypoxia-Induced Expression of Vascular Endothelial Growth Factor by Retinal Cells is a Common Factor in Neovascularizing Ocular Disease," Laboratory Investigation, 1995, vol. 72, No. 6, pp. 638-645.
Pietras, K. et al., "Inhibition of PDGF Receptor Signaling in Tumor Stroma Enhances Antitumor Effect of Chemotherapy," Cancer Research, Oct. 1, 2002, vol. 62, pp. 5476-5484.
Pietras, K. et al., "Inhibition of Platelet-derived Growth Factor Receptors Reduces Interstitial Hypertension and increases Transcapillary Transport in Tumors," Cancer Research, Apr. 1, 2001, vol. 61, pp. 2929-2934.
Seetharam, L. et al., "A unique transduction from FLT tyrosine kinase, a receptor for vascular endothelial growth factor VEGF," Oncogene, 1995, vol. 10, pp. 135-147.
Shaheen, R. M. et al., "Antiangiogenic Therapy targeting the Tyrosine Kinase Receptor for Vascular Endothelial Growth Factor Receptor Inhibits the Growth of Colon Cancer Liver Metastasis and Induces Tumor and Endothelial Cell Apoptosis," Cancer Research, Nov. 1, 1990, vol. 59, pp. 5412-5416.
Shaheen, R. M. et al., "Tyrosine Kinase Inhibition of Multiple Angiogenic Growth Factor Receptors Improves Survival in Mice Bearing Colon Cancer Liver Metastases by Inhibition of Endothelial Cell Survival Mechanisms," Cancer Research, Feb. 15, 2001, vol. 61, pp. 1464-1468.

(56) References Cited

OTHER PUBLICATIONS

Shemirani, B. et al., "Hypoxic induction of HIF-1alpha and VEGF expression in head and neck squamous cell carcinoma lines is mediated by stress activated protein kinase," Oral Oncology, 2002, vol. 38, pp. 251-257.

Shweiki, D. et al., "Vascular endothelial growth factor induced by hypoxia may mediate hypoxia-initiated angiogenesis," Nature, Oct. 29, 1992, vol. 359, pp. 843-845.

Simon, C. et al., "The p38 SAPK Pathway Regulates the Expression of the MMP-9 Collagenase via AP-1-Dependent Promoter Activation," Experimental Cell Research, 2001, vol. 271, pp. 344-355.

Skobe, M. et al., "Induction of tumor lymphangiogenesis by VEGF-C promotes breast cancer metastasis," Nature Medicine, Feb. 2001, vol. 7, No. 2, pp. 192-198.

Skobe, M. et al., "Tumorgenic conversion of immortal human keratinocytes through stromal cell activation," Proc. Natl. Sci., Feb. 1998, vol. 95, pp. 1050-1055.

Soskic, V. et al., "Functional Proteomics Analysis of Signal Transduction Pathways of the Platelet-derived Growth Factor β Receptor," Biochemistry, 1999, vol. 38, pp. 1757-1764.

Stacker, S. A. et al., "VEFR-D promotes the metastatic spread of tumor cells via the lymphatics," Nature Medicine, Feb. 2001, vol. 7, No. 2, pp. 186-191.

Sundberg, C. et al., "Tumor Cell and Connective Tissue Cell Interactions in Human Colorectal Adenocarcinoma," American Journal of Pathology, Aug. 1997, vol. 151, No. 2, pp. 479-492.

Vignaud, J. M. et al., "The Role of Platelet-derived Growth Factor Production by Tumor-associated Macrophages in Tumor Stroma Formation in Lung Cancer," Cancer Research, Oct. 15, 1994, vol. 54, pp. 5455-5463.

Waltenberger, J. et al., "Different Signal Transduction Properties of KDR and Flt1, Two Receptors for Vascular Endothelial Growth Factor," The Journal of Biological Chemistry, Oct. 28, 1994, vol. 269, No. 43, pp. 26988-26995.

Wang, J. et al., "Cell Proliferation in Human Soft Tissue Tumors Correlates with Platelet-derived Growth Factor B Chain Expression: An Immunohistochemical and in Situ Hybridization Study," Cancer Research, Jan. 15, 1994, vol. 54, pp. 560-564.

Westermarck, J. et al., "Activation of Fibroblast Collagenase-1 Expression by Tumor Cells of Squamous Cell Carcinomas Is Mediated by p28 Mitogen-activated Protein Kinase and c-Jun $NH_2$-terminal Kinase-$2^1$," Cancer Research, Dec. 15, 2000, vol. 60, pp. 7156-7162.

\* cited by examiner

SUBSTITUTED PYRIMIDINE DERIVATIVES USEFUL IN THE TREATMENT OF CANCER AND OTHER DISORDERS

This application claims the benefit of U.S. Provisional Application No. 60/752,200, filed Dec. 21, 2005.

FIELD OF THE INVENTION

This invention relates to novel compounds, pharmaceutical compositions containing such compounds and the use of those compounds or compositions for treating hyper-proliferative and angiogenesis disorders, as a sole agent or in combination with other active ingredients, e.g., cytotoxic therapies.

BACKGROUND OF THE INVENTION

Activation of the ras signal transduction pathway indicates a cascade of events that have a profound impact on cellular proliferation, differentiation, and transformation. Raf kinase, a downstream effector of ras, is recognized as a key mediator of these signals from cell surface receptors to the cell nucleus (Lowy, D. R.; Willumsen, B. M. *Ann. Rev. Biochem.* 1993, 62, 851; Bos, J. L. *Cancer Res.* 1989, 49, 4682). It has been shown that inhibiting the effect of active ras by inhibiting the raf kinase signaling pathway by administration of deactivating antibodies to raf kinase or by co-expression of dominant negative raf kinase or dominant negative MEK, the substrate of raf kinase, leads to the reversion of transformed cells to the normal growth phenotype (see: Daum et al. *Trends Biochem. Sci.* 1994, 19, 474-80; Fridman et al. *J. Biol. Chem.* 1994, 269, 30105-8. Kolch et al. (*Nature* 1991, 349, 426-28) have further indicated that inhibition of raf expression by antisense RNA blocks cell proliferation in membrane-associated oncogenes. Similarly, inhibition of raf kinase (by antisense oligodeoxynucleotides) has been correlated in vitro and in vivo with inhibition of the growth of a variety of human tumor types (Monia et al., *Nat. Med.* 1996, 2, 668-75). Some examples of small molecule inhibitors of Raf kinase activity are important agents for the treatment of cancer. (Naumann, U.; Eisenmann-Tappe, I.; Rapp, U. R. *Recent Results Cancer Res.* 1997, 143, 237; Monia, B. P.; Johnston, J. F.; Geiger, T.; Muller, M.; Fabbro, D. *Nature Medicine* 1996, 2, 668).

To support progressive tumor growth beyond the size of 1-2 mm$^3$, it is recognized that tumor cells require a functional stroma, a support structure consisting of fibroblast, smooth muscle cells, endothelial cells, extracellular matrix proteins, and soluble factors (Folkman, J., *Semin Oncol,* 2002. 29(6 Suppl 16), 15-8). Tumors induce the formation of stromal tissues through the secretion of soluble growth factors such as PDGF and transforming growth factor-beta (TGF-beta), which in turn stimulate the secretion of complimentary factors by host cells such as fibroblast growth factor (FGF), epidermal growth factor (EGF), and vascular endothelial growth factor (VEGF). These stimulatory factors induce the formation of new blood vessels, or angiogenesis, which brings oxygen and nutrients to the tumor and allows it to grow and provides a route for metastasis. It is believed some therapies directed at inhibiting stroma formation will inhibit the growth of epithelial tumors from a wide variety of Histological types. (George, D. *Semin Oncol,* 2001. 28(5 Suppl 17), 27-33; Shaheen, R. M., et al., *Cancer Res,* 2001. 61(4); 1464-8; Shaheen, R. M., et al. *Cancer Res,* 1999. 59(21), 5412-6). However, because of the complex nature and the multiple growth factors involved in angiogenesis process and tumor progression, an agent targeting a single pathway may have limited efficacy. It is desirable to provide treatment against a number of key signaling pathways utilized by tumors to induce angiogenesis in the host stroma. These include PDGF, a potent stimulator of stroma formation (Ostman, A. and C. H. Heldin, *Adv Cancer Res,* 2001, 80, 1-38), FGF, a chemoattractant and mitogen for fibroblasts and endothelial cells, and VEGF, a potent regulator of vascularization.

PDGF is another key regulator of stromal formation which is secreted by many tumors in a paracrine fashion and is believed to promote the growth of fibroblasts, smooth muscle and endothelial cells, promoting stroma formation and angiogenesis. PDGF was originally identified as the v-sis oncogene product of the simian sarcoma virus (Heldin, C. H., et al., *J Cell Sci Suppl,* 1985, 3, 65-76). The growth factor is made up of two peptide chains, referred to as A or B chains which share 60% homology in their primary amino acid sequence. The chains are disulfide cross linked to form the 30 kDa mature protein composed of either AA, BB or AB homo- or heterodimers. PDGF is found at high levels in platelets, and is expressed by endothelial cells and vascular smooth muscle cells. In addition, the production of PDGF is up regulated under low oxygen conditions such as those found in poorly vascularized tumor tissue (Kourembanas, S., et al., *Kidney Int,* 1997, 51(2), 438-43). PDGF binds with high affinity to the PDGF receptor, a 1106 amino acid 124 kDa transmembrane tyrosine kinase receptor (Heldin, C. H., A. Ostman, and L. Ronnstrand, *Biochim Biophys Acta,* 1998. 1378(1), 79-113). PDGFR is found as homo- or heterodimer chains which have 30% homology overall in their amino acid sequence and 64% homology between their kinase domains (Heldin, C. H., et al. *Embo J,* 1988, 7(5), 1387-93). PDGFR is a member of a family of tyrosine kinase receptors with split kinase domains that includes VEGFR2 (KDR), VEGFR3 (Flt4), c-Kit, and FLT3. The PDGF receptor is expressed primarily on fibroblast, smooth muscle cells, and pericytes and to a lesser extent on neurons, kidney mesangial, Leydig, and Schwann cells of the central nervous system. Upon binding to the receptor, PDGF induces receptor dimerization and undergoes auto- and trans-phosphorylation of tyrosine residues which increase the receptors' kinase activity and promotes the recruitment of downstream effectors through the activation of SH2 protein binding domains. A number of signaling molecules form complexes with activated PDGFR including PI-3-kinase, phospholipase C-gamma, src and GAP (GTPase activating protein for p21-ras) (Soskic, V., et al. *Biochemistry,* 1999, 38(6), 1757-64). Through the activation of PI-3-kinase, PDGF activates the Rho signaling pathway inducing cell motility and migration, and through the activation of GAP, induces mitogenesis through the activation of p21-ras and the MAPK signaling pathway.

In adults, it is believed the major function of PDGF is to facilitate and increase the rate of wound healing and to maintain blood vessel homeostasis (Baker, E. A. and D. J. Leaper, *Wound Repair Regen,* 2000. 8(5), 392-8; Vu, J., A. Moon, and H. R. Kim, *Biochem Biophys Res Commun,* 2001. 282(3), 697-700). PDGF is found at high concentrations in platelets and is a potent chemoattractant for fibroblast, smooth muscle cells, neutrophils and macrophages. In addition to its role in wound healing PDGF is known to help maintain vascular homeostasis. During the development of new blood vessels, PDGF recruits pericytes and smooth muscle cells that are needed for the structural integrity of the vessels. PDGF is thought to play a similar role during tumor neovascularization. As part of its role in angiogenesis PDGF controls interstitial fluid pressure, regulating the permeability of vessels through its regulation of the interaction between connective tissue cells and the extracellular matrix. Inhibiting PDGFR activity can lower interstitial pressure and facilitate the influx of cytotoxics into tumors improving the anti-tumor efficacy of these agents (Pietras, K., et al. *Cancer Res*, 2002. 62(19), 5476-84; Pietras, K., et al. *Cancer Res*, to 2001. 61(7), 2929-34).

PDGF can promote tumor growth through either the paracrine or autocrine stimulation of PDGFR receptors on stromal cells or tumor cells directly, or through the amplification of the receptor or activation of the receptor by recombination. Over expressed PDGF can transform human melanoma cells and keratinocytes (Forsberg, K., et al. *Proc Natl Aced Sci USA.*, 1993. 90(2), 393-7; Skobe, M. and N. E. Fusenig, *Proc Natl Aced Sci USA*, 1998. 95(3), 1050-5), two cell types that do not express PDGF receptors, presumably by the direct effect of PDGF on stroma formation and induction of angiogenesis. This paracrine stimulation of tumor stroma is also observed in carcinomas of the colon, lung, breast, and prostate (Bhardwaj, B., et al. *Clin Cancer Res*, 1996, 2(4), 773-82; Nakanishi, K., et al. *Mod Pathol*, 1997, 10(4), 341-7; Sundberg, C., et al. *Am J Pathol*, 1997, 151(2), 479-92; Lindmark, G., et al. *Lab Invest*, 1993, 69(6), 682-9; Vignaud, J. M., et al, *Cancer Res*, 1994, 54(20), 5455-63) where the tumors express PDGF, but not the receptor. The autocrine stimulation of tumor cell growth, where a large faction of tumors analyzed express both the ligand PDGF and the receptor, has been reported in glioblastomas (Fleming, T. P., et al. *Cancer Res*, 1992, 52(16), 4550-3), soft tissue sarcomas (Wang, J., M. D. Coltrera, and A. M. Gown, *Cancer Res*, 1994, 54(2), 560-4) and cancers of the ovary (Henriksen, R., et al. *Cancer Res*, 1993, 53(19), 4550-4), prostate (Fudge, K., C. Y. Wang, and M. E. Stearns, *Mod Pathol*, 1994, 7(5), 549-54), pancreas (Funa, K., et al. *Cancer Res*, 1990, 50(3), 748-53) and lung (Antoniades, H. N., et al., *Proc Natl Acad Sci USA*, 1992, 89(9), 3942-6). Ligand independent activation of the receptor is found to a lesser extent but has been reported in chronic myelomonocytic leukemia (CMML) where the a chromosomal translocation event forms a fusion protein between the Ets-like transcription factor TEL and the PDGF receptor. In addition, activating mutations in PDGFR have been found in gastrointestinal stromal tumors in which c-Kit activation is not involved (Heinrich, M. C., et al., *Science*, 2003, 9, 9).

Certain PDGFR inhibitors will interfere with tumor stromal development and are believed to inhibit tumor growth and metastasis.

Another major regulator of angiogenesis and vasculogenesis in both embryonic development and some angiogenic-dependent diseases is vascular endothelial growth factor (VEGF; also called vascular permeability factor, VPF). VEGF represents a family of isoforms of mitogens existing in homodimeric forms due to alternative RNA splicing. The VEGF isoforms are reported to be highly specific for vascular endothelial cells (for reviews, see: Farrara et al. *Endocr. Rev.* 1992, 93, 18; Neufield et al. *FASEB J.* 1999, 13, 9).

VEGF expression is reported to be induced by hypoxia (Shweiki et al. *Nature* 1992, 359, 843), as well as by a variety of cytokines and growth factors, such as interleukin-1, interleukin-6, epidermal growth factor and transforming growth factor. To date, VEGF and the VEGF family members have been reported to bind to one or more of three transmembrane receptor tyrosine kinases (Mustonen et al. *J. Cell Biol.*, 1995, 129, 895), VEGF receptor-1 (also known as flt-1 (fms-like tyrosine kinase-1)), VEGFR-2 (also known as kinase insert domain containing receptor (KDR); the murine analogue of KDR is known as fetal liver kinase-1 (flk-1)), and VEGFR-3 (also known as flt-4). KDR and flt-1 have been shown to have different signal transduction properties (Waltenberger et al. *J. Biol. Chem.* 1994, 269, 26988); Park et al. *Oncogene* 1995, 10, 135). Thus, KDR undergoes strong ligand-dependant tyrosine phosphorylation in intact cells, whereas flt-1 displays a weak response. Thus, binding to KDR is believed to be a critical requirement for induction of the full spectrum of VEGF-mediated biological responses.

In vivo, VEGF plays a central role in vasculogenesis, and induces angiogenesis and permeabilization of blood vessels. Deregulated VEGF expression contributes to the development of a number of diseases that are characterized by abnormal angiogenesis and/or hyperpermeability processes. It is believed regulation of the VEGF-mediated signal transduction cascade by some agents can provide a useful mode for control of abnormal angiogenesis and/or hyperpermeability processes.

Angiogenesis is regarded as an important prerequisite for growth of tumors beyond about 1-2 mm. Oxygen and nutrients may be supplied to cells in tumors smaller than this limit through diffusion. However, it is believed every tumor is dependent on angiogenesis for continued growth after it has reached a certain size. Tumorigenic cells within hypoxic regions of tumors respond by stimulation of VEGF production, which triggers activation of quiescent endothelial cells to stimulate new blood vessel formation. (Shweiki et al. *Proc. Nat'l. Acad. Sci.*, 1995, 92, 768). In addition, VEGF production in tumor regions where there is no angiogenesis may proceed through the ras signal transduction pathway (Grugel et al. *J. Biol. Chem.*, 1995, 270, 25915; Rak et al. *Cancer Res.* 1995, 55, 4575). In situ hybridization studies have demonstrated VEGF mRNA is strongly upregulated in a wide variety of human tumors, including lung (Mattern et al. *Br. J. Cancer* 1996, 73, 931), thyroid (Viglietto et al. *Oncogene* 1995, 11, 1569), breast (Brown et al. *Human Pathol.* 1995, 26, 86), gastrointestinal tract (Brown et al. *Cancer Res.* 1993, 53, 4727; Suzuki et al. *Cancer Res.* 1996, 56, 3004), kidney and bladder (Brown et al. *Am. J. Pathol.* 1993, 143I, 1255), ovary (Olson et al. *Cancer Res.* 1994, 54, 1255), and cervical (Guidi et al. *J. Nat'l Cancer Inst.* 1995, 87, 12137) carcinomas, as well as angiosarcoma (Hashimoto et al. *Lab. Invest.* 1995; 73, 859) and several intracranial tumors (Plate et al. *Nature* 1992, 359, 845; Phillips et al. *Int. J. Oncol.* 1993, 2, 913; Berkman et al. *J. Clin. Invest.*, 1993, 91, 153). Neutralizing monoclonal antibodies to KDR have been shown to be efficacious in blocking tumor angiogenesis (Kim et al. *Nature* 1993, 362, 841; Rockwell et al. *Mol. Cell. Differ.* 1995, 3, 315).

Over expression of VEGF, for example under conditions of extreme hypoxia, can lead to intraocular angiogenesis, resulting in hyperproliferation of blood vessels, leading eventually to blindness. Such a cascade of events has been observed for a number of retinopathies, including diabetic retinopathy, ischemic retinal-vein occlusion, and retinopathy of prematurity (Aiello et al. *New Engl. J. Med.* 1994, 331, 1480; Peer et al. *Lab. Invest.* 1995, 72, 638), and age-related macular degeneration (AMD; see, Lopez et al. *Invest. Opththalmol. Vis. Sci.* 1996, 37, 855).

In rheumatoid arthritis (RA), the in-growth of vascular pannus may be mediated by production of angiogenic factors. Levels of immunoreactive VEGF are high in the synovial fluid of RA patients, while VEGF levels were low in the synovial fluid of patients with other forms of arthritis of with degenerative joint disease (Koch et al. *J. Immunol.* 1994, 152, 4149). The angiogenesis inhibitor AGM-170 has been shown to prevent neovascularization of the joint in the rat collagen arthritis model (Peacock et al. *J. Exper. Med.* 1992, 175, 1135).

Increased VEGF expression has also been shown in psoriatic skin, as well as bullous disorders associated with subepidermal blister formation, such as bullous pemphigoid, erythema multiforme, and dermatitis herpetiformis (Brown et al. *J. Invest. Dermatol.* 1995, 104, 744).

The vascular endothelial growth factors (VEGF, VEGF-C, VEGF-D) and their receptors (VEGFR2, VEGFR3) are not only key regulators of tumor angiogenesis, but also lymphangiogenesis. VEGF, VEGF-C and VEGF-D are expressed in most tumors, primarily during periods of tumor growth and, often at substantially increased levels. VEGF expression is stimulated by hypoxia, cytokines, oncogenes such as ras, or by inactivation of tumor suppressor genes (McMahon, G. *Oncologist* 2000, 5(Suppl. 1), 3-10; McDonald, N. Q.; Hendrickson, W. A. *Cell* 1993, 73, 421-424)

The biological activities of the VEGFs are mediated through binding to their receptors. VEGFR3 (also called Flt-4) is predominantly expressed on lymphatic endothelium in normal adult tissues. VEGFR3 function is needed for new lymphatic vessel formation, but not for maintenance of the pre-existing lymphatics. VEGFR3 is also upregulated on blood vessel endothelium in tumors. Recently VEGF-C and VEGF-D, ligands for VEGFR3, have been identified as regulators of lymphangiogenesis in mammals. Lymphangiogenesis induced by tumor-associated lymphangiogenic factors could promote the growth of new vessels into the tumor, providing tumor cells access to systemic circulation. Cells that invade the lymphatics could find their way into the bloodstream via the thoracic duct. Tumor expression studies have allowed a direct comparison of VEGF-C, VEGF-D and VEGFR3 expression with clinicopathological factors that relate directly to the ability of primary tumors to spread (e.g., lymph node involvement, lymphatic invasion, secondary metastases, and disease-free survival). In many instances, these studies demonstrate a statistical correlation between the expression of lymphangiogenic factors and the ability of a primary solid tumor to metastasize (Skobe, M. et al, *Nature Med.* 2001, 7(2), 192-198; Stacker, S. A. et al. *Nature Med.* 2001, 7(2), 186-191; Makinen, T. et al. *Nature Med.* 2001, 7(2), 199-205; Mandriota, S. J. et al. *EMBO J.* 2001, 20(4), 672-82; Karpanen, T. et al. *Cancer Res.* 2001, 61(5), 1786-90; Kubo, H. et al. *Blood* 2000, 96(2), 546-53).

Hypoxia appears to be an important stimulus for VEGF production in malignant cells. Activation of p38 MAP kinase is required for VEGF induction by tumor cells in response to hypoxia (Blaschke, F. et al. *Biochem. Biophys. Res. Commun.* 2002, 296, 890-896; Shemirani, B. et al. *Oral Oncology* 2002, 38, 251-257). In addition to its involvement in angiogenesis through regulation of VEGF secretion, p38 MAP kinase promotes malignant cell invasion, and migration of different tumor types through regulation of collagenase activity and urokinase plasminogen activator expression (Laferriere, J. et al. *J. Biol. Chem.* 2001, 276, 33762-33772; Westermarck, J. et al. *Cancer Res.* 2000, 60, 7156-7162; Huang, S. et al. *J. Biol. Chem.* 2000, 275, 12266-12272; Simon, C. et al. *Exp. Cell Res.* 2001, 271, 344-355).

Some diarylureas have been described as having activity as serine-threonine kinase and/or as tyrosine kinase inhibitors. The utility of these diarylureas as an active ingredient in pharmaceutical compositions for the treatment of cancer, angiogenesis disorders, and inflammatory disorders has been demonstrated. See Redman et al., *Bioorg. Med. Chem. Lett.* 2001, 11, 9-12; Smith et al., *Bioorg. Med. Chem. Lett.* 2001, 11, 2775-2778; Dumas et al., *Bioorg. Med. Chem. Lett.* 2000, 10, 2047-2050; Dumas et al., *Bioorg. Med. Chem. Lett.* 2000, 10, 2051-2054; Ranges et al., *Book of Abstracts, 220th ACS National Meeting*, Washington, D.C., USA, MEDI 149; Dumas et al., *Bioorg. Med. Chem. Lett.* 2002, 12, 1559-1562; Lowinger et al., *Clin. Cancer Res.* 2000, 6(suppl.), 335; Lyons et al., *Endocr.-Relat. Cancer* 2001, 8, 219-225; Riedl et al., *Book of Abstracts, 92nd AACR Meeting*; New Orleans, La., USA, abstract 4956; Khire et al., *Book of Abstracts, 93rd AACR Meeting*, San Francisco, Calif., USA, abstract 4211; Lowinger et al., *Curr. Pharm. Design* 2002, 8, 99-110; Regan et al., *J. to Med. Chem.* 2002, 45, 2994-3008; Pargellis et al., *Nature Struct. Biol.* 2002, 9(4), 268-272; Carter et al., *Book of Abstracts, 92nd AACR Meeting*, New Orleans, La., USA, abstract 4954; Vincent et al., *Book Of Abstracts, 38th ASCO Meeting*, Orlando, Fla., USA, abstract 1900; Hilger et al., *Book of Abstracts, 38th ASCO Meeting*, Orlando, Fla., USA, abstract 1916; Moore et al., *Book of Abstracts, 38th ASCO Meeting*, Orlando, Fla., USA, abstract 1816; Strumberg et al., *Book of Abstracts, 38th ASCO Meeting*, Orlando, Fla., USA, abstract 121; Madwed J B: *Book of Abstracts, Protein Kinases Novel Target Identification and Validation for Therapeutic Development*, San Diego, Calif., USA, March 2002; Roberts et al., *Book of Abstracts, 38th ASCO Meeting*, Orlando, Fla., USA, abstract 473; Tolcher et al., *Book of Abstracts, 38th ASCO Meeting*, Orlando, Fla., USA, abstract 334; and Karp et al., *Book of Abstracts, 38th AACR Meeting*, San Francisco, Calif., USA, abstract 2753.

Despite the advancements in the art, there remains a need for cancer treatments and anti-cancer compounds.

DESCRIPTION OF THE INVENTION

The present invention pertains to:
(i) novel compounds of formula (I) below, salts, metabolites, prodrugs and diastereoisomeric forms thereof (both isolated stereoisomers and mixtures of stereoisomers), collectively referred to herein as the "compounds of the invention";
(ii) pharmaceutical compositions containing compounds of this invention; and
(iii) use of compounds of this invention or pharmaceutical compositions containing compounds of this invention for treating diseases, e.g., hyper-proliferative and angiogenesis disorders, as a sole agent or in combination with other anti-cancer agents.

Formula I is as follows:

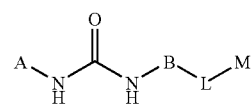

I

A is pyrimidine,
optionally substituted with 1 to 3 substituents which are independently $R^1$, $OR^1$, $S(O)_pR^1$, $C(O)R^1$, $C(O)OR^1$, $C(O)NR^1R^2$, halogen, hydroxy, amino, cyano, or nitro;
B is phenyl, naphthyl, or pyridyl, optionally substituted with 1 to 4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, or nitro.
B is preferably phenyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, or nitro.
L is a bridging group which is:
(a) —$(CH_2)_m$—O—$(CH_2)_r$—,
(b) —$(CH_2)_m$—$(CH_2)_r$—,
(c) —$(CH_2)_m$—C(O)—$(CH_2)_r$—,
(d) —$(CH_2)_m$—$NR^3$—$(CH_2)_r$—, (e) —$(CH_2)_m$—$NR^3C(O)$—$(CH_2)_l$—,
(f) —$(CH_2)_m$—S—$(CH_2)_l$—, or
(g) —$(CH_2)_m$—$C(O)NR^3$—$(CH_2)_l$—.

The integers m and l are independently selected from 0-4 and are typically selected from 0-2. The group —$(CH_2)_m$—$(CH_2)_l$— defines a single bond where m and l are 0.

L is most preferably —O— or —S—.

M is a pyridine or pyrimidine ring, optionally substituted with 1-3 substituents which are independently selected from:
(1) $C_1$-$C_5$ linear or branched alkyl;
(2) $C_1$-$C_5$ linear or branched haloalkyl;
(3) $C_1$-$C_3$ alkoxy;
(4) hydroxy;
(5) amino;
(6) $C_1$-$C_3$ alkylamino;
(7) $C_1$-$C_6$ dialkylamino;
(8) halogen;
(9) nitro;
(10) $C(O)NR^4R^5$;
(11) $C(O)OR^4$;
(12) $C(O)R^4$;
(13) CN;
(14) $C(S)NR^4R^5$;
(15a) $C(O)NR^7$—$NR^4R^5$;
(15b) $C(O)NR^7$—$R^4C(O)NR^4R^5$;
(16) tetrazolyl;
(17) imidazolyl;
(18) imidazoline-2-yl;
(19) 1,3,4-oxadiazoline-2-yl;
(20) 1,3-thiazoline-2-yl;
(21) 5-thioxo-4,5-dihydro-1,3,4-thiazoline-2-yl;
(22) 5-oxo-4,5-dihydro-1,3,4-oxadiazoline-2-yl; or
(23) a group of the formula

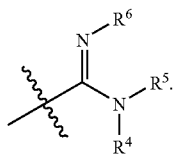

M is preferably pyridine, optionally substituted with 1-3 substituents which are independently selected from the groups (1) to (13) cited above.

Each of $R^1$, $R^2$, $R^3$, $R^4$ and $R^5$ is independently
(a) hydrogen,
(b) $C_1$-$C_5$ linear, branched, or cyclic alkyl,
(c) phenyl,
(d) $C_1$-$C_3$ phenyl-alkyl,
(e) up to per-halo substituted $C_1$-$C_5$ linear or branched alkyl, or
(f) —$(CH_2)_q$—X.

The substituent X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms selected from the group consisting of O, N and S.

In addition, $R^4$ and $R^5$ taken together may form a 5 or 6 membered aliphatic ring, which may be interrupted by an atom selected from N, O or S. This is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, oxo, carboxy, amino, $C_1$-$C_3$ alkylamino, $C_1$-$C_6$ dialkylamino, halogen, cyano, or nitro.

$R^6$ is independently:
(a) hydrogen,
(b) $C_1$-$C_5$ linear, branched, or cyclic alkyl,
(c) cyano,
(d) nitro,
(e) up to per-halo substituted $C_1$-$C_5$ linear or branched alkyl. or
(f) —$C(O)R^7$, where $R^7$ is $C_1$-$C_5$ linear, branched, or cyclic alkyl.

$R^6$ is preferably independently:
(a) hydrogen,
(b) $C_1$-$C_5$ linear, branched, or cyclic alkyl, or
(c) cyano or
(d) nitro, and most preferably, $R^6$ is independently:
(a) hydrogen,
(b) $C_1$-$C_5$ linear, branched, or cyclic alkyl, or
(c) cyano.

$R^7$ is hydrogen, or $C_1$-$C_5$ linear, branched, or cyclic alkyl.

The variable q is an integer 0, 1, 2, 3, or 4. The variable p is an integer 0, 1, or 2. When any moiety is "substituted", it can have up to the highest number of indicated substituents, and each substituent can be located at any available position on the moiety and can be attached through any available atom on the substituent. "Any available position" means any position on the moiety that is chemically accessible through means known in the art or taught herein and that does not create an unduly unstable molecule. When there are two or more substituents on any moiety, each substituent is defined independently of any other substituent and can, accordingly, be the same or different.

The term "optionally substituted" means that the moiety so modified may be either unsubstituted, or substituted with the identified substituent(s).

It is understood that since M is pyridine, the term "hydroxy" as a pyridine substituent includes 2-, 3-, and 4-hydroxypyridine, but also includes those structures referred to in the art as 1-oxo-pyridine, 1-hydroxy-pyridine and pyridine N-oxide.

Where the plural form of the word compounds, salts, and the like, is used herein, this is taken to mean also a single compound, salt, or the like.

The term "$C_1$-$C_5$alkyl", as used herein, means straight or branched chain alkyl groups having from one to five carbon atoms, which may be linear or branched with single or multiple branching. Such groups include methyl, ethyl, n-propyl, isopropyl, n-butyl, isobutyl, sec-butyl, tert-butyl, and the like.

The term "$C_1$-$C_5$ haloalkyl", as used herein, means a saturated hydrocarbon radical having up to five carbon atoms, which is substituted with a least one halogen atom, up to perhalo. The radical may be linear or branched with single or multiple branching. The halo substituent(s) include fluoro, chloro, bromo, or iodo. Fluoro, chloro and bromo are preferred, and fluoro and chloro are more preferred. The halogen substituent(s) can be located on any available carbon. When more than one halogen substituent is present on this moiety, they may be the same or different. Examples of such halogenated alkyl substituents include but are not limited to chloromethyl, dichloromethyl, trichloromethyl, fluoromethyl, difluoromethyl, trifluoromethyl, 2,2,2-trifluoroethyl, and 1,1, 2,2-tetrafluoroethyl, and the like.

The term "$C_1$-$C_3$ alkoxy", as used herein, means a straight or branched chain alkoxy group having from one to three saturated carbon atoms which may be linear or branched with single or multiple branching, and includes such groups as methoxy, ethoxy, n-propoxy, isopropoxy, and the like. It also includes halogenated groups such as 2,2-dichloroethoxy, trifluoromethoxy, and the like.

Halo or halogen means fluoro, chloro, bromo, or iodo. Fluoro, chloro and bromo are preferred, and fluoro and chloro are more preferred.

The term "$C_1$-$C_3$alkylamine", as used herein, means methylamino, ethylamino, propylamino or isopropylamino.

Examples of $C_1$-$C_6$ dialkylamine include but are not limited to diethylamino, ethyl-isopropylamino, methyl-isobutylamino and dihexylamino.

The term "heteroaryl", as used herein, refers to both monocyclic and bicyclic heteroaryl rings. Monocyclic heteroaryl means an aromatic monocyclic rings having 5 to 6 ring atoms, at least one of which is a hetero atom selected from N, O and S, the remaining atoms being carbon. When more than one hetero atom is present in the moiety, they are selected independently from the other(s) so that they May be the same or different. Monocyclic heteroaryl rings include, but are not limited to pyrrole, furan, thiophene, imidazole, pyrazole, thiazole, oxazole, isoxazole, isothiazole, triazole, tetrazole, thiadiazole, oxadiazole, pyridine, pyrimidine, pyridazine, pyrazine, and triazine.

The term "bicyclic heteroaryl", as used herein, means fused bicyclic moieties where one of the rings is chosen from the monocyclic heteroaryl rings described above and the second ring is either benzene or another monocyclic heteroaryl ring described above. When both rings in the bicyclic moiety are heteroaryl rings, they may be the same or different, as long as they are chemically accessible by means known in the art. Bicyclic heteroaryl rings include synthetically accessible 5-5, 5-6, or 6-6 fused bicyclic aromatic structures including, for example but not by way of limitation, benzoxazole (fused benzene and oxazole), indazole (fused benzene and pyrazole), quinoline (fused phenyl and pyridine), quinazoline (fused pyrimidine and benzene), imidazopyrimidine (fused imidazole and pyrimidine), naphthyridine (two fused pyridines), and the like.

The term "5 or 6 membered heterocyclic ring, containing at least one atom selected from oxygen, nitrogen and sulfur, which is saturated, partially saturated, or aromatic" includes, by no way of limitation, tetrahydropyrane, tetrahydrofurane, 1,3-dioxolane, 1,4-dioxane, morpholine; thiomorpholine, piperazine, piperidine, piperidinone, tetrahydropyrimidone, pentamethylene sulfide, tetramethylene sulfide, dihydropyrane, dihydrofurane, dihydrothiophene, pyrrole, furan, thiophene, imidazole, pyrazole, thiazole, oxazole, isoxazole, Isothiazole, triazole, pyridine, pyrimidine, pyridazine, pyrazine, triazine, and the like.

Non-limiting examples of group of the formula

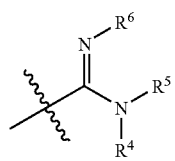

where $R^4$ and $R^5$ taken together may form a 5 or 6 membered aliphatic ring, which may be interrupted by an atom selected from N, O or S, which is optionally substituted include:

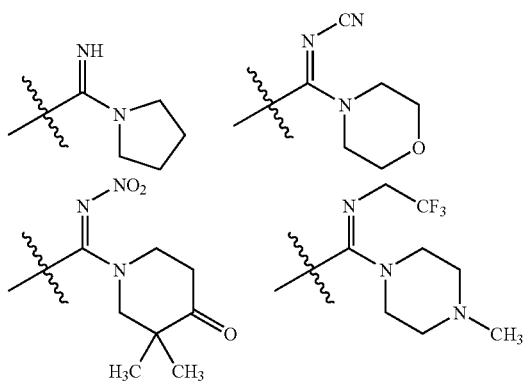

The term "$C_1$-$C_3$ phenyl-alkyl" includes, by no way of limitation, 3-phenyl-propyl, phenyl-1-methyl-ethyl. Substituted examples include 2-[2-chlorophenyl]ethyl, 3,4-dimethylphenyl-methyl, and the like.

The compounds of Formula I may contain one or more asymmetric centers, depending upon the location and nature of the various substituents desired.

Asymmetric carbon atoms may be present in the (R) or (S) configuration or (R,S) configuration. In certain instances, asymmetry may also be present due to restricted rotation about a given bond, for example, the central bond adjoining two substituted aromatic rings of the specified compounds. Substituents on a ring may also be present in either cis or trans form. It is intended that all such configurations (including enantiomers and diastereomers), are included within the scope of the present invention. Preferred compounds are those with the absolute configuration of the compound of Formula I which produces the more desirable biological activity. Separated, pure or partially purified isomers or racemic mixtures of the compounds of this invention are also included within the scope of the present invention. The purification of said isomers and the separation of said isomeric mixtures can be accomplished by standard techniques known in the art.

The optical isomers can be obtained by resolution of the racemic mixtures according to conventional processes, for example, by the formation of diastereoisomeric salts is using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formula I can likewise be obtained by chiral syntheses utilizing optically active starting materials.

The present invention also relates to useful forms of the compounds as disclosed herein, such as pharmaceutically acceptable salts, metabolites and prodrugs of all the compounds Formula (I). The term "pharmaceutically acceptable salt" refers to a relatively non-toxic, inorganic or organic acid addition salt of a compound of the present invention. For example, see S. M: Berge, et al. "Pharmaceutical Salts," *J. Pharm. Sci.* 1977, 66, 1-19. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an to appropriate base to form, e.g., sodium, potassium, calcium, magnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

Representative salts of the compounds of this invention include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, palmoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and stearyl chlorides, bromides and iodides, aralkyl halides like benzyl and phenethyl bromides and others.

Certain compounds of this invention can be further modified with labile functional groups that are cleaved after in vivo administration to furnish the parent active agent to and the pharmacologically inactive derivatizing (functional) group. These derivatives, commonly referred to as prodrugs, can be used, for example, to alter the physicochemical properties of the active agent, to target the active agent to a specific tissue, to alter the pharmacokinetic and pharmacodynamic properties of the active agent, and to reduce undesirable side effects Prodrugs of the invention include, e.g., the esters of appropriate compounds of this invention are well-tolerated, pharmaceutically acceptable esters such as alkyl esters including methyl, ethyl, propyl, isopropyl, butyl, isobutyl or pentyl esters. Additional esters such as phenyl-$C_1$-$C_5$ alkyl may be used, although methyl ester is preferred.

Methods for synthesizing prodrugs are described in the following reviews on the subject, which are incorporated herein by reference for their description of these methods:

Higuchi, T.; Stella, V. eds. *Prodrugs As Novel Drug Delivery Systems*. ACS Symposium Series. American Chemical Society: Washington, D.C. (1975).

Roche, E. B. *Design of Biopharmaceutical Properties through Prodrugs and Analogs*. American Pharmaceutical Association: Washington, D.C. (1977).

Sinkula, A. A.; Yalkowsky, S. H. *J Pharm Sci.* 1975, 64, 181-210.

Stella, V. J.; Charman, W. N. Naringrekar, V. H. *Drugs* 1985, 29, 455-473.

Bundgaard, H., ed. *Design of Prodrugs*. Elsevier: New York (1985).

Stella, V. J.; Himmelstein, K. J. *J. Med. Chem.* 1980, 23, 1275-1282.

Han, H-K; Amidon, G. L. *AAPS Pharmsci* 2000, 2, 1-11.

Denny, W. A. *Eur. J. Med. Chem.* 2001, 36, 577-595.

Wermuth, C. G. in Wermuth, C. G. ed. *The Practice of Medicinal Chemistry* Academic Press: San Diego (1996), 697-715.

Balant, L. P.; Doelker, E. in Wolff, M. E. ed. *Burgers Medicinal Chemistry And Drug Discovery* John Wiley & Sons: New York (1997), 949-982.

The metabolites of the compounds of this invention include oxidized derivatives of the compounds of Formula I, wherein one or more of the nitrogens are substituted with a hydroxy group; which includes derivatives where the nitrogen atom of the pyridine group is in the oxide form, referred to in the art as 1-oxo-pyridine or has a hydroxy substituent, referred to in the art as 1-hydroxy-pyridine.

Compounds of interest within the scope of formula I are of formula (III) including the salts, metabolites, prodrugs and diastereoisomeric forms thereof,

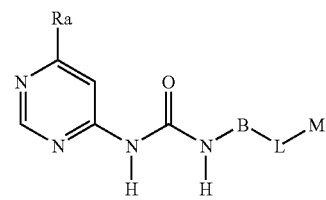

(III)

wherein Ra is $R^1$, $OR^1$ or cyano; and B, L and M are as defined above.

Another group of compounds of interest within the scope of formula I are of formula (IV) including the salts, metabolites, prodrugs and diastereoisomeric forms thereof,

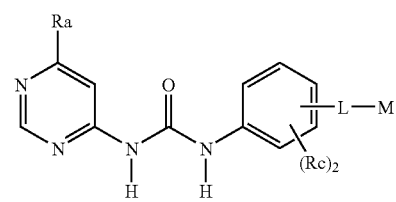

(IV)

wherein Ra is $R^1$, $OR^1$ or cyano; each Rc is independently hydrogen, halogen, $C_1$-$C_3$ linear or branched alkyl, $C_1$-$C_3$ linear or branched haloalkyl, $C_1$-$C_3$ alkoxy or hydroxy; and L and M are as defined above.

Another group of compounds of interest within the scope of formula I are of formula (V) including the salts, metabolites, prodrugs and diastereoisomeric forms thereof,

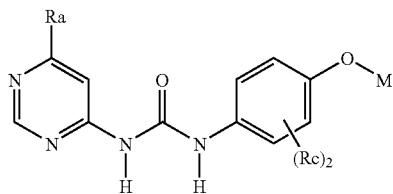

(V)

wherein Ra, Rc and M is are as defined above. In groups of interest M is pyridine in formulae III, IV and V, and is typically substituted by $C(O)NR^4R^5$ or CN. In certain groups of interest, $C(O)NR^4R^5$ is $C(O)NHCH_3$ or $C(O)NH_2$.

A further group of compounds of interest are of formula (II) including the salts, metabolites; prodrugs and diastereoisomeric forms thereof,

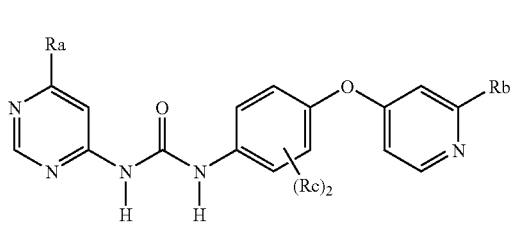

(II)

wherein Ra; Rc are as defined above and
Rb is
(1) $C_1$-$C_5$ linear or branched alkyl;
(2) $C_1$-$C_5$ linear or branched haloalkyl;
(3) $C_1$-$C_3$ alkoxy;
(4) hydroxy;
(5) amino;
(6) $C_1$-$C_3$ alkylamino;
(7) $C_1$-$C_6$ dialkylamino;
(8) halogen;
(9) nitro;
(10) $C(O)NR^4R^5$;
(11) $C(O)OR^4$;
(12) $C(O)R^4$;
(13) CN;
(14) $C(S)NR^4R^5$;
(15) $C(O)NR^7$—$R^4C(O)NR^4R^5$; or
(16) hydrogen;
with each of $R^1$, $R^4$, $R^5$ and $R^7$ independently as defined above.

For a group of compounds of Formula II of interest, Rb is $C_1$-$C_5$ linear or branched alkyl; $C_1$-$C_3$ alkoxy; halogen; $C(O)NR^4R^5$; CN; $C(S)NR^4R^5$ or $C(O)NR^7$—$R^4C(O)NR^4R^5$. For another group of compounds of formula II of interest, Rb is $C_1$-$C_5$ linear or branched alkyl; halogen; $C(O)NR^4R^5$ or CN. In a further sub-groups, Rb is $C(O)NR^4R^5$ or CN or Rb is only $C(O)NR^4R^5$.

For the compounds of formula II and the groups thereof mentioned above, there are sub-groups where each Rc, independently, is hydrogen or fluorine and Rb is $C(O)NHCH_3$ or $C(O)NH_2$.

General Preparative Methods

The particular process to be utilized in the preparation of the compounds used in this embodiment of the invention depends upon the specific compound desired. Such factors as the selection of the specific substituents play a role in the path to be followed in the preparation of the specific compounds of this invention. Those factors are readily recognized by one of ordinary skill in the art.

The compounds of the invention may be prepared by use of known chemical reactions and procedures. Nevertheless, the following general preparative methods are presented to aid the reader in synthesizing the compounds of the present invention, with more detailed particular examples being presented below in the experimental section describing the working examples.

All variable groups of these methods are as described in the generic description if they are not specifically defined below. When a variable group or substituent with a given symbol is used more than once in a given structure, it is to be understood that each of these groups or substituents may be independently varied within the range of definitions for that symbol. It is recognized that compounds of the invention with each claimed optional functional group cannot be prepared with each of the below-listed methods. Within the scope of each method optional substituents are used which are stable to the reaction conditions, or the functional groups which may participate in the reactions are present in protected form where necessary, and the removal of such protective groups is completed at appropriate stages by methods well known to those skilled in the art.

The compounds of the invention can be made according to conventional chemical methods, and/or as disclosed below, from starting materials which are either commercially available or producible according to routine, conventional chemical methods. General methods for the preparation of the compounds are given below, and the preparation of representative compounds is specifically illustrated in examples.

General Method 1

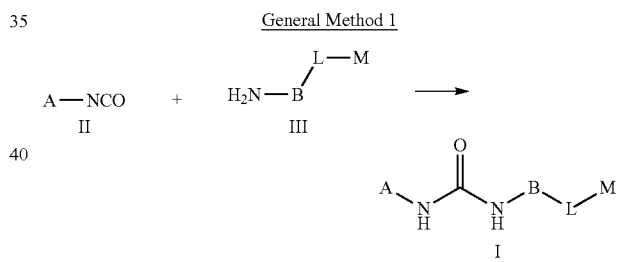

The compounds (I) can be synthesized according to the reaction sequence shown in the General Method 1 above. Thus, the compounds (I) can be synthesized by reacting amino compounds (III) with isocyanate compounds (II).

The compounds (II) are commercially available or can be synthesized according to methods commonly known to those skilled in the art, e.g. from treatment of an amine with phosgene or a phosgene equivalent such as trichloromethyl chloroformate (diphosgene), bis(trichloromethyl)carbonate (triphosgene), or N,N'-carbonyldiimidazole (CDI); or, alternatively by a Curtius-type rearrangement of an amide, or a carboxylic acid derivative, such as an ester, an acid halide or an anhydride. The compounds (III) are commercially available or can be synthesized according methods commonly known to those skilled in the art.

Alternatively, compounds of Formula (I) can be prepared according to general method 2, where aminopyrimidines of formula (IV) and amino compounds of formula (III) are coupled together to form a urea of Formula (I), with the use of a coupling agent such as carbonyldiimidazole, phosgene, diphosgene, triphosgene, and the like. The coupling step may be performed in an inert solvent such as dioxane, diethylether, dichloromethane, chloroform, tetrahydrofuran, toluene, and the like, at a temperature selected between 0° C. and reflux. This coupling may be achieved using these reagents alone, or, in the presence of an organic or inorganic base as described in the art.

General Method 2

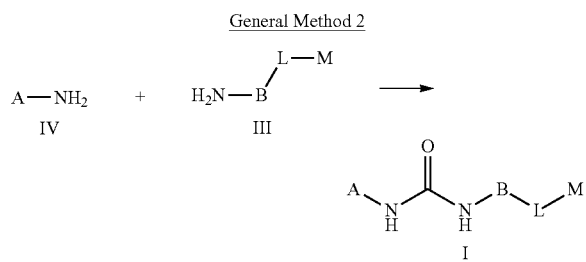

In addition specific preparations of diaryl ureas are already described in the patent literature, and can be adapted to the compounds of the present invention. For example, Miller S. et al, "Inhibition of p38 Kinase using Symmetrical and Unsymmetrical Diphenyl Ureas" PCT Int. Appl. WO 99 32463, Miller, S et al. "Inhibition of raf Kinase using Symmetrical and Unsymmetrical Substituted Diphenyl Ureas" PCT Int. Appl., WO 99 32436, Dumas, J. et al., "Inhibition of p38 Kinase Activity using Substituted Heterocyclic Ureas" PCT Int. Appl., WO 99 32111, Dumas, J. et al., "Method for the Treatment of Neoplasm by Inhibition of raf Kinase using N-Heteroaryl-N'-(hetero)arylureas" PCT Int. Appl., WO 99 32106, Dumas, J. et al., "Inhibition of p38 Kinase Activity using Aryl- and Heteroaryl-Substituted Heterocyclic Ureas" PCT Int. Appl., WO 99 32110, Dumas, J., et al., "Inhibition of raf Kinase using Aryl- and Heteroaryl-Substituted Heterocyclic Ureas" PCT Int. Appl., WO 99 32455, Riedl, B., et al., "O-Carboxy Aryl Substituted Diphenyl Ureas as raf Kinase Inhibitors" PCT Int. Appl., WO 00 42012, Riedl, B., et al., "O-Carboxy Aryl Substituted Diphenyl Ureas as p38 Kinase Inhibitors" PCT Int. Appl., WO 00 41698, Dumas, J. et al. "Heteroaryl ureas containing nitrogen hetero-atoms as p38 kinase inhibitors" U.S. Pat. Appl. Publ., US 20020065296, Dumas, J. et al. "Preparation of N-aryl-N'-[(acylphenoxy) phenyl]ureas as raf kinase inhibitors" PCT Int. Appl., WO 02 62763, Dumas, J. et al. "inhibition of raf kinase using quinolyl, isoquinolyl or pyridyl ureas" PCT Int. Appl., WO 02 85857, Dumas, J. et al. "Preparation of quinolyl, isoquinolyl or pyridyl-ureas as inhibitors of raf kinase for the treatment of tumors and/or cancerous cell growth" U.S. Pat. Appl. Publ., US 20020165394. All the preceding patent applications are hereby incorporated by reference.

The reaction of the compounds (II) with (III) is carried out preferably in a solvent. Suitable solvents comprise the customary organic solvents which are inert under the reaction conditions. Non-limiting examples include ethers such as diethyl ether, dioxane, tetrahydrofuran, 1,2-dimethoxy ethane; hydrocarbons such as benzene, toluene, xylene, hexane, cyclohexane, mineral oil fractions; halogenated hydrocarbons such as dichloromethane, trichloromethane, carbon tetrachloride, dichloroethane, trichloroethylene, chlorobenzene; alcohols such as methanol, ethanol, n-propanol, isopropanol; esters such as ethyl acetate; ketones such as acetone; nitrites such as acetonitrile; heteroaromatics such as pyridine; polar solvents such as dimethyl formamide and hexamethyl phosphoric acid tris-amide; and mixtures of the above-mentioned solvents. Toluene, benzene, and dichloromethane are preferred.

The compounds (III) are generally employed in an amount of from 1 to 3 mol per mol of compounds (II); an equimolar amount or slight excess of compounds (III) is preferred.

The reaction of the compounds (II) with (III) is generally carried out within a relatively wide temperature range. In general, they are carried out in a range of from −20 to 200° C., preferably from 0 to 100° C., and more preferably from 25 to 50° C. The steps of this reaction are generally carried out under atmospheric pressure. However, it is also possible to carry them out under superatmospheric pressure or under reduced pressure (for example, in a range of from 0.5 to 5 bar). The reaction time can generally be varied within a relatively wide range. In general, the reaction is finished after a period of from 2 to 24 hours, preferably from 6 to 12 hours.

Synthetic transformations that may be employed in the synthesis of compounds of Formula I and in the synthesis of intermediates involved in the synthesis of compounds of Formula I are known by or accessible to one skilled in the art. Collections of synthetic transformations may be found in compilations, such as:

J. March. *Advanced Organic Chemistry,* 4th ed.; John Wiley: New York (1992)

R. C. Larock. *Comprehensive Organic Transformations,* 2nd ed.; Wiley-VCH: New York (1999)

F. A. Carey; R. J. Sundberg. *Advanced Organic Chemistry,* 2nd ed.; Plenum Press: New York (1984)

T. W. Greene; P. G. M. Wuts. *Protective Groups in Organic Synthesis,* 3rd ed.; John Wiley: New York (1999)

L. S. Hegedus. *Transition Metals in the Synthesis of Complex Organic Molecules,* 2nd ed., University Science Books: Mill Valley, Calif. (1994)

L. A. Paquette, Ed. *The Encyclopedia of Reagents for Organic Synthesis*; John Wiley: New York (1994)

A. R. Katritzky; O. Meth-Cohn; C. W. Rees, Eds. *Comprehensive Organic Functional Group Transformations*; Pergamon Press: Oxford, UK (1995)

G. Wilkinson; F. G A. Stone; E. W. Abel, Eds. *Comprehensive Organometallic Chemistry*; Pergamon Press: Oxford, UK (1982)

B. M. Trost; I. Fleming. *Comprehensive Organic Synthesis*; Pergamon Press: Oxford, UK (1991)

A. R. Katritzky; C. W. Rees Eds. *Comprehensive Heterocylic Chemistry*; Pergamon Press: Oxford, UK (1984)

A. R. Katritzky; C. W. Rees; E. F. V. Scriven, Eds. *Comprehensive Heterocylic Chemistry II*; Pergamon Press: Oxford, UK (1996)

C. Hansch; P. G. Sammes; J. B. Taylor, Eds. *Comprehensive Medicinal Chemistry*: Pergamon Press: Oxford, UK (1990).

In addition, recurring reviews of synthetic methodology and related topics include *Organic Reactions*; John Wiley: New York; *Organic Syntheses*; John Wiley: New York; *Reagents for Organic Synthesis*: John Wiley: New York; *The Total Synthesis of Natural Products*; John Wiley: New York; *The Organic Chemistry of Drug Synthesis*; John Wiley New York; *Annual Reports in Organic Synthesis*; Academic Press: San Diego Calif.; and *Methoden der Organischen Chemie* (Houben-Weyl); Thieme: Stuttgart, Germany. Furthermore, databases of synthetic transformations include *Chemical Abstracts,* which may be searched using either CAS OnLine or SciFinder, *Handbuch der Organischen Chemie* (Beilstein), which may be searched using SpotFire, and REACCS.

The preparation of the compounds of the present invention is further illustrated in Examples 1-13.

Compositions of the Compounds of this Invention

This invention also relates to pharmaceutical compositions containing one or more compounds of the present invention.

These compositions can be utilized to achieve the desired pharmacological effect by administration to a patient in need thereof. A patient, for the purpose of this invention, is a mammal, including a human, in need of treatment for the particular condition or disease.

The active compounds of the present invention can act systemically and/or locally. For this purpose, they can be administered in a suitable manner, such as for example by oral, parenteral, pulmonary, nasal, sublingual, lingual, buccal, rectal, dermal, transdermal, conjunctival or aural administration or in the form of an implant or stent. The active compound can be administered in forms suitable for these modes of administration.

Suitable forms of oral administration are those according to the prior art which function by releasing the active compound rapidly and/or in a modified or controlled manner and which contain the active compound in a crystalline and/or amorphous and/or dissolved form, such as for example tablets (which are uncoated or coated, for example with enteric coatings or coatings which dissolve after a delay in time or insoluble coatings which control the release of the active compound), tablets or films/wafers which disintegrate rapidly in the oral cavity or films/lyophilisates, capsules (e.g. hard or soft gelatin capsules), dragées, pellets, powders, emulsions, suspensions and solutions.

Parenteral administration can be carried out by avoiding an absorption step (e.g. by intravenous, intraarterial, intracardial, intraspinal or intralumbar administration) or by including absorption (e.g. by intramuscular, subcutaneous, intracutaneous or intraperitoneal administration). Suitable parenteral administration forms are for example injection and infusion formulations in the form of solutions, suspensions, emulsions, lyophilisates and sterile powders.

Suitable forms of administration for the other modes of administration are for example inhalation devices (such as for example powder inhalers, nebulizers), nasal drops, solutions and sprays; tablets or films/wafers for lingual, sublingual or buccal administration or capsules, suppositories, ear and eye preparations, vaginal capsules, aqueous suspensions (lotions or shaking mixtures), lipophilic suspensions, ointments, creams, transdermal or therapeutic systems, milky lotions, pastes, foams, dusting powders, implants or stents.

The active compounds can be converted into the above mentioned forms of administration in a manner known to the skilled man and in accordance with the prior art using inert, non-toxic, pharmaceutically suitable auxiliaries. The latter include for example excipients (e.g. microcrystalline cellulose, lactose, mannitol, etc.), solvents (e.g. liquid polyethylene glycols), emulsifiers and dispersants or wetting agents (e.g. sodium dodecyl sulphate, polyoxysorbitan oleate etc.), binders (e.g. polyvinyl pyrrolidone), synthetic and/or natural polymers (e.g. albumin), stabilizers (e.g. antioxidants, such as, for example, ascorbic acid), dyes (e.g. inorganic pigments such as iron oxides) or taste- and/or odor-corrective agents.

Method of Treating Hyper-proliferative Disorders

The present invention also relates to a method for using the compounds of Formula I and pharmaceutical compositions containing them to treat mammalian hyper-proliferative disorders, including cancer. The term "hyper-proliferative disorders" and/or "cancer" not only refers to solid tumors, such as cancers of the breast, respiratory tract, brain, reproductive organs, digestive tract, urinary tract, eye, liver, skin, head and neck, thyroid, parathyroid and their distant metastases, but also includes lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypophthalmic glioma, cerebellar and cerebral astrocytoma, medulloblastoma, ependymoma, as well as neuroectodermal and pineal tumor.

Tumors of the male reproductive organs include, but are not limited to prostate and testicular cancer. Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallbladder, gastric, pancreatic, rectal, small intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, cutaneous T-cell lymphoma, Hodgkin's disease, and lymphoma of the central nervous system.

Sarcomas include, but are not limited to sarcoma of the soft tissue, fibrosarcoma, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering the compounds and pharmaceutical compositions of the present invention.

Any raf or VEGFR polypeptide can be modulated in accordance with present invention, including both wild-type and mutant forms. Raf or raf-1 kinase is a family of serine/threonine kinases which comprise at least three family members, A-Raf, B-Raf, and c-raf or Raf-1. See, e.g., Dhillon and Kolch, Arch. Biochem. Biophys., 404:3-9, 2002. C-raf and B-Raf are preferred targets for compounds of the present invention. Activating B-Raf mutations (e.g., V599E mutant) have been identified in various cancers, including melanoma, and the compounds described herein can be utilized to inhibit their activity. Mutations, include mutations in K-RAS; mutations in the BRAF gene, such as mutations at position 599, such as V599E, and/or positions 461, 462, 463, 465, 468, 593, 596, 60, etc., which are associated with cancers, such as melanoma.

VEGFR-2, as indicated above, plays a role in angiogenesis, and therefore inhibiting it is useful to treat tumors and other diseases associated with neovasculature, including rheumatoid arthritis, osteoarthritis, asthma, pulmonary fibrosis, age-related macular degeneration (ARMD), diabetic retinopathy, macular degeneration, and retinopathy of prematurity (ROP), endometriosis, cancer, Coats' disease, peripheral retinal neovascularization, neovascular glaucoma, psoriasis, retrolental fibroplasias, angiofibroma, inflammation, etc.

Methods of the present invention include modulating tumor cell proliferation, including inhibiting cell proliferation. The latter indicates that the growth and/or differentiation of tumor cells is reduced, decreased, diminished, slowed, etc. The term "proliferation" includes any process which relates to cell growth and division, and includes differentiation and apoptosis. As discussed above, raf kinases play a key role in the activation of the cytoplasmic signaling cascade involved in cell proliferation, differentiation, and apoptosis. For example, studies have found that inhibiting c-raf-1 by antisense oligonucleotides can block cell proliferation (see above). Any amount of inhibition is considered therapeutic.

Additionally, the present invention relates to methods of screening patients to determine their susceptibility to compounds of the present invention. For example, the presenting invention relates to methods of selecting subjects having a disease for treatment with a compound of formula I, comprising, one or more of the following steps in any effective order, e.g., measuring the expression or activity of Raf, VEGFR-2, or other kinase receptors, in a sample obtained from a subject having a disease, and administering said compound of formula I to subjects who are identified as having high levels of expression or activity, where said compound is a compound of formula I of claim 1.

The term "susceptibility" is used broadly to indicate, e.g., ability to respond, toxicity or other adverse effects, etc. For example, the invention relates to methods of determining whether a condition can be modulated by a compound disclosed herein, comprising measuring the expression or activity of Raf, VEGFR-2, or other kinase proteins in cells having said condition. The results can be used to determine or predict whether a subject will respond to a compound of the present invention. For example, where the condition is a tumor, the methods can be used to predict whether the tumor is susceptible to compounds of the present invention. By the term "susceptible," it is meant that tumor can be treated with it, e.g., causing tumor regression or cell death, inhibiting cell proliferation, inhibiting tumor growth, inhibiting tumor metastasis, etc.

Whether a condition, such as a tumor, is susceptible to a compound of the present invention can be determined routinely. For instance, cells or tissues (e.g., tumor cells, a biopsy sample, etc.) that exhibit the condition can be assayed for the presence and/or activity of Raf, VEGFR-2, or other kinase proteins. When high levels of expression and/or activity are identified, this can indicate that the subject will respond to, and benefit from, a compound of the present invention. Levels of gene expression (e.g., mRNA levels), gene amplification, or gene product activity (e.g., tyrosine kinase activity) can be utilized to characterize the state of the cell with respect to the corresponding gene and signaling pathway. For example, the target genes of the present invention possess tyrosine kinase activity, and therefore kinase activity can be used to assess the cell or tissue state. In the example below, activity was measured by looking at the levels of substrate phosphorylated by it. This can be done quantitatively (e.g., using isotopes, spectroscopy, etc.) or semi-quantitatively as in the example where the levels were assessed visually and assigned a level of intensity from +1 to +4. A cell or tissue which has a high level of phosphorylated substrate (and a high number of cells exhibiting the heightened activity) can be considered to have a high level of kinase activity, and therefore be a candidate for therapy with a compound of the present invention. More than one activity can be assessed, and the results from several targets can be utilized in deciding whether a subject's condition (e.g., a tumor) will be responsive to a compound of the present invention.

High levels of target activity can be relative to a control or other standard. For instance, in the example below, high levels of activity were with reference to a cell type (stromal) in the tissue section which normally does not express substantial levels of the target gene. High levels can therefore be where cells express a statistically higher amount of measured activity or phosphorylated substrate than the standard or control used as a comparison. High levels can also be where 25% or more cells express the target activity.

The method can further comprise a step of comparing the expression in a sample with a normal control, or expression in a sample obtained from normal or unaffected tissue. Comparing can be done manually, against a standard, in an electronic form (e.g., against a database), etc. The normal control can be a standard sample that is provided with the assay; it can be obtained from adjacent, but unaffected, tissue from the same patient; or, it can be pre-determined values, etc. Gene expression, protein expression (e.g., abundance in a cell), protein activity (e.g., kinase activity), etc., can be determined.

For instance, a biopsy from a cancer patient can be assayed for the presence, quantity, and/or activity of Raf, VEGFR-2, or other kinase proteins. Increased expression or activity of one or more of these can indicate that the cancer can be targeted for treatment by a compound of the present invention. For example, raf activity can be monitored by its ability to initiate the cascade leading to ERK phosphorylation (i.e., raf/MEK/ERK), resulting in phospho-ERK. Increased phospho-ERK levels in a cancer shows that its raf activity is elevated, suggesting the use of compounds of the present invention to treat it. In addition to biopsy samples, phospho-ERK (other markers) can also be measured in other body fluids, such as serum, blood, cerebral spinal fluid, urine, etc., such as in peripheral blood lymphocytes (PBLs). For the latter, inhibition of ERK phosphorylation can be measured following activation with phorbol myristate acetate using antibodies as described in the examples below.

In addition, patients having cancer can be selected and monitored on the basis of whether the tissue is experiencing neovascularization, and how much. This can be assessed as discussed above, e.g., using immunohistochemistry for vessel markers (e.g., CD31), circulating levels of a VGFR ligand, etc.

Patient selection and monitoring can also be made on the basis of the appearance in a body fluid (such as blood) above normal levels of the shedded ectodomains derived from the various receptors, including the extracellular portions of VEGFR-2 or other kinase receptors. Detection methods can be carried out routinely, e.g., using antibodies which specifically bind to the extracellular domain.

Measuring expression includes determining or detecting the amount of the polypeptide present in a cell or shed by it, as well as measuring the underlying mRNA, where the quantity of mRNA present is considered to reflect the quantity of polypeptide manufactured by the cell. Furthermore, the genes for Raf, VEGFR-2, and other kinase proteins can be analyzed to determine whether there is a gene defect responsible for aberrant expression or polypeptide activity. Genes sequences are publically available; e.g., NM_004333 *Homo sapiens* v-raf murine sarcoma viral oncogene homolog B1 (BRAF); NM_002253 *Homo sapiens* VEGFR2.

The present invention also provides methods of assessing the efficacy of a compound of the present invention in treating a disease, comprising one or more of the following steps in any effective order, e.g., measuring the expression or activity of Raf, VEGFR-2, or other kinase proteins in a sample obtained from said subject who has been treated with a compound of the present invention, and determining the effects of said compound on said expression or activity. The measuring step can be carried out as described already.

For instance, biopsy samples can be removed from patients who have been treated with a compound of the present invention, and then assayed for the presence and/or activity of the mentioned signaling molecules. As discussed above, decreased levels of phospho-ERK in the cancer tissue (e.g., compared to a normal tissue or before treatment) indicate that the compound is exerting in vivo efficacy and a therapeutic effect.

Determining the effects of the compound on expression or activity includes performing a comparison step between a tissue sample and a control, or other type of standard. Examples of standards that can be used, include, but are not limited to, a tissue sample prior to treatment, a tissue sample from an unaffected tissue or from an unaffected region of the affected tissue (e.g., from a region of the tissue which is not transformed, cancerous, etc.), etc. A standard can also be a value, or range of values, that is representative of normal levels of, expression that have been established for that marker. The comparison can also be made between samples collected from at least two different timepoints during the treatment regimen with a compound of the present invention. For example, samples can be collected from various times after initiation of the drug treatment, and analysis of expression and/or activity levels can be used to monitor the progress/prognosis of the subject, e.g., how the subject is responding to the drug regimen. Any timepoint can be used, e.g., daily, twice a week, weekly, every two weeks, every month, yearly, a plurality of timepoints (at least 2, 3, 4, 8, 12, etc.).

The method can be used to determine appropriate dosages and dosing is regimens, e.g., how much compound to administer and at what frequency to administer it. By monitoring its effect on the signaling molecules in the tissue, the clinician can determine the appropriate treatment protocol and whether it is achieving the desired effect, e.g., on modulating or inhibiting the signal transduction pathway. For instance, if the compound is not effective in knocking down the amounts of a marker, such as phospho-ERK, the dosage can be increased in the patient or given more frequently. Similarly, dosages and/or frequency can be reduced when it is shown that the compound is effective in knocking down the levels of phospho-ERK or other marker for the disease state. Since the compounds can be administered in combination with others treatments, e.g., radiation, chemotherapy, and other agents, the monitoring of the subject can be used to assess the combined effects of the treatment regimen on the progress of the disease.

The total amount of the active ingredient (compounds of Formula I) to be administered to a patient will generally range from about 0.01 mg/kg to about 50 mg/kg body weight per day. Based upon standard laboratory techniques known to evaluate compounds useful for the treatment of hyper-proliferative disorders, by standard toxicity tests and by standard pharmacological assays for the determination of treatment of the conditions identified above in mammals, and by comparison of these results with the results of known medicaments that are used to treat these conditions, the effective dosage of the compounds and pharmaceutical compositions of this invention can readily be determined by those skilled in the art. The amount of the administered active ingredient can vary widely according to such considerations as the particular compound and dosage unit employed, the mode and time of administration, the period of treatment, the age, sex, and general condition of the patient treated, the nature and extent of the condition treated, the rate of drug metabolism and excretion, the potential drug combinations and drug-drug interactions, and the like.

The compounds and pharmaceutical compositions of this invention can be administered as the sole agent or in combination with one or more other therapies where the combination causes no unacceptable adverse effects. For example, they can be combined with cytotoxic agents, signal transduction inhibitors, or with other anti-cancer agents or therapies, as well as with admixtures and combinations thereof.

In one embodiment, the compounds and pharmaceutical compositions of the present invention can be combined with cytotoxic anti-cancer agents. Examples of such agents can be found in the 11$^{th}$ Edition of the *Merck Index* (1996). These agents include, by no way of limitation, asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, and vindesine.

Other cytotoxic drugs suitable for use with the compounds and pharmaceutical compositions of the invention include, but are not limited to, those compounds acknowledged to be used in the treatment of neoplastic diseases in *Goodman and Gilman's The Pharmacological Basis of Therapeutics* (Ninth Edition, 1996, McGraw-Hill). These agents include, by no way of limitation, aminoglutethimide, L-asparaginase, azathioprine, 5-azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, and vinorelbine.

Other cytotoxic anti-cancer agents suitable for use in combination with the compounds and pharmaceutical compositions of the invention also include newly discovered cytotoxic principles such as oxaliplatin, gemcitabine, capecitabine, epothilone and its natural or synthetic derivatives, temozolomide (Quinn et al., *J. Clin. Oncology* 2003, 21(4), 646-651), tositumomab (Bexxar), trabedectin (Vidal et al., *Proceedings of the American Society for Clinical Oncology* 2004, 23, abstract 3181), and the inhibitors of the kinesin spindle protein Eg5 (Wood et al., *Curr. Opin. Pharmacol.* 2001, 1, 370-377).

In another embodiment, the compounds and pharmaceutical compositions of the present invention can be combined with other signal transduction inhibitors. Of particular interest are signal transduction inhibitors which target the EGFR family, such as EGFR, HER-2, and HER-4 (Raymond et al., *Drugs* 2000, 60 (Suppl. 1), 15-23; Harari et al., *Oncogene* 2000, 19 (53), 6102-6114), and their respective ligands. Examples of such agents include, by no way of limitation, antibody therapies such as Herceptin (trastuzumab), Erbitux (cetuximab), and pertuzumab. Examples of such therapies also include, by no way of limitation, small-molecule kinase inhibitors such as ZD-1839/Iressa (Baselga et al., *Drugs* 2000, 60 (Suppl. 1), 33-40), OSI-774/Tarceva (Pollack et al.

J. Pharm. Exp. Ther. 1999, 291(2), 739-748), CI-1033 (Bridges, Curr. Med. Chem. 1999, 6, 825-843), GW-2016 (Lackey et al., 92$^{nd}$ AACR Meeting, New Orleans, Mar. 24-28, 2001, abstract 4582), CP-724,714. Wall et al., Proceedings of the American Society for Clinical Oncology 2004, 23, abstract 3122), HKI-272 (Rabindran et al., Cancer Res. 2004, 64, 3958-3965), and EKB-569 (Greenberger et al., 11$^{th}$ NCI-EORTC-AACR Symposium on New Drugs in Cancer Therapy, Amsterdam, Nov. 7-10, 2000, abstract 388).

In another embodiment, the compounds and pharmaceutical compositions of the present invention can be combined with other signal transduction inhibitors targeting receptor kinases of the split-kinase domain families (VEGFR, FGFR, PDGFR, flt-3, c-kit, c-fms, and the like), and their respective ligands. These agents include, by no way of limitation, antibodies such as Avastin (bevacizumab). These agents also include, by no way of limitation, small-molecule inhibitors such as STI-571/Gleevec (Zvelebil, Curr. Opin. Oncol., Endocr. Metab. Invest. Drugs 2000, 2(1), 74-82), PTK-787 (Wood et al., Cancer Res. 2000, 60(8), 2178-2189), SU-11248 (Demetri et al., Proceedings of the American Society for Clinical Oncology 2004, 23, abstract 3001), ZD-6474 (Hennequin et al., 92$^{nd}$ AACR Meeting, New Orleans, Mar. 24-28, 2001, abstract 3152), AG-13736 (Herbst et al., Clin. Cancer Res. 2003, 9, 16 (suppl 1), abstract C253), KRN-951 (Taguchi et al., 95$^{th}$ AACR-Meeting, Orlando, Fla., 2004, abstract 2575), CP-547,632 (Beebe et al., Cancer Res. 2003, 63, 7301-7309), CP-673,451 (Roberts et al., Proceedings of the American Association of Cancer Research 2004, 45, abstract 3989), CHIR-258 (Lee et al., Proceedings of the American Association of Cancer Research 2004, 45, abstract 2130), MLN-518 (Shen et al., Blood 2003, 102, 11, abstract 476), and AZD-2171 (Hennequin et al., Proceedings of the American Association of Cancer Research 2004, 45, abstract 4539).

In another embodiment, the compounds and pharmaceutical compositions of the present invention can be combined with inhibitors of the Raf/MEK/ERK transduction pathway (Avruch et al., Recent Prog. Horm. Res. 2001, 56, 127-155), or the PKB (akt) pathway (Lawlor et al., J. Cell Sci. 2001, 114, 2903-2910). These include, by no way of limitation, PD-325901 (Sebolt-Leopold et al., Proceedings of the American Association of Cancer Research 2004, 45, abstract 4003), and ARRY-142886 (Wallace et al., Proceedings of the American Association of Cancer Research 2004, 45, abstract 3891).

In another embodiment, the compounds and pharmaceutical compositions of the present invention can be combined with inhibitors of histone deacetylase. Examples of such agents include, by no way of limitation, suberoylanilide hydroxamic acid (SAHAi), LAQ-824 (Ottmann et al., Proceedings of the American Society for Clinical Oncology 2004, 23, abstract 3024), LBH-589 (Beck et al., Proceedings of the American Society for Clinical Oncology 2004, 23, abstract 3025), MS-275 (Ryan et al., Proceedings of the American Association of Cancer Research 2004, 45, abstract 2452), and FR-901228 (Piekarz et al., Proceedings of the American Society for Clinical Oncology 2004, 23, abstract 3028).

In another embodiment, the compounds and pharmaceutical compositions of the present invention can be combined with other anti-cancer agents such as proteasome inhibitors, and m-TOR inhibitors. These include, by no way of limitation, bortezomib (Mackay et al., Proceedings of the American Society for Clinical Oncology 2004, 23, Abstract 3109), and CCI-779 (Wu et al., Proceedings of the American Association of Cancer Research 2004, 45, abstract 3849).

Generally, the use of cytotoxic and/or cytostatic anti-cancer agents in combination with the compounds or pharmaceutical compositions of the present invention will serve to:
(1) yield better efficacy in reducing the growth of a tumor or even eliminate the tumor as compared to administration of either agent alone,
(2) provide for the administration of lesser amounts of the administered agents,
(3) provide for a chemotherapeutic treatment protocol that is well tolerated in the patient with fewer deleterious pharmacological complications than observed with single agent chemotherapies and certain other combined therapies,
(4) provide for treating a broader spectrum of different cancer types in mammals, especially humans,
(5) provide for a higher response rate among treated patients,
(6) provide for a longer survival time among treated patients compared to standard chemotherapy treatments,
(7) provide a longer time for tumor progression, and/or
(8) yield efficacy and tolerability results at least as good as those of the agents is used alone, compared to known instances where other cancer agent combinations produce antagonistic effects.

It is believed that one skilled in the art, using the preceding information and information available in the art, can utilize the present invention to its fullest extent.

It should be apparent to one of ordinary skill in the art that changes and modifications can be made to this invention without departing from the spirit or scope of the invention as it is set forth herein.

All publications, applications and patents cited above and below are incorporated herein by reference.

EXAMPLES

Abbreviations used in this specification
DBU 1,8-diazabicyclo[5.4.0]undec-7-ene
DMF N,N-dimethyl formamide
DCM Dichloromethane
DCE 1,2-dichloroethane
DMSO dimethyl sulphoxide
HPLC High pressure liquid chromatography
MPLC Medium pressure liquid chromatography
LC-MS liquid chromatography-coupled mass spectroscopy
RT retention time
MP melting point
NMR nuclear resonance spectroscopy
TLC thin layer chromatography
ES electrospray
DMA N,N-dimethylacetamide
HRMS high resolution mass spectroscopy
CDI 1,1'-carbonyldiimidazole
HOBT 1-hydroxybenzotriazole
EDCI 1-[3-(dimethylamino)propyl]-3-ethylcarbodiimide hydrochloride
TMSCl Trimethylsilyl chloride
m-CPBA 3-chloroperbenzoic acid
HEPES N-(2-hydroxyethyl)-piperazine-N'-(2-ethane sulphonic acid)
Tris/hydrochloric acid tris(hydroxymethyl)-aminomethane hydrochloride
™Triton X-100® tert.-octyl-phenoxypolyethoxyethanol, Rohm & Haas, USA The yield percentages of the following examples refer to the starting component which was used in the lowest molar amount.

LC-MS conditions: HPLC-electrospray mass spectra (HPLC ES-MS) were obtained using a Gilson HPLC system equipped with two Gilson 306 pumps, a Gilson 215 Autosampler, a Gilson diode array detector, a YMC Pro C-18 column (2×23 mm, 120 A), and a Micromass LCZ single quadrupole mass spectrometer with z-spray electrospray ionization. Spectra were scanned from 120-1000 amu over 2 seconds. ELSD (Evaporative Light Scattering Detector) data was also acquired as an analog channel. Gradient elution was used with Buffer A as 2% acetonitrile in water with 0.02% TFA and Buffer B as 2% water in Acetonitrile with 0.02% TFA at 1.5 mL/min. Samples were eluted as follows: 90% A for 0.5 minutes ramped to 95% B over 3.5 minutes and held at 95% B for 0.5 minutes and then the column is brought back to initial conditions over 0.1 minutes. Total run time is 4.8 minutes.

Preparation of
6-Trifluoromethyl-pyrimidin-4-ylamine

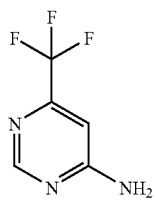

The procedure was derived from methods described in U.S. Pat. No. 5,756,275 and WO 02/38569. In a 250 mL round bottom flask, 6-trifluoromethyl-4-pyrimidinol (10 g, 60.9 mmol) was dissolved in 70 mL phosphorus oxychloride (0.73 mol). The solution was heated at reflux for 7 h. The cooled reaction solution was then added gradually to 200 mL 30% ammonium hydroxide, and the resulting mixture was stirred overnight at room temperature. The reaction mixture was extracted with ethyl acetate (2×100 mL), and the combined extracts were dried (MgSO$_4$) and evaporated in vacuo to give 6-trifluoromethyl-pyrimidin-4-ylamine (1.4 g, yield 14%) as a white solid. $^1$H NMR (400 MHz, DMSO-d$_6$) δ 8.50 (s, 1 H), 7.60 (broad s, 2 H), 6.90 (s, 1 H); LC-MS m/z 164.1 [M+H]$^+$.

Example 1

4-{3-fluoro-4-[3-(6-trifluoromethylpyrimidin-4-yl)ureido]phenoxy}pyridine-2-carboxylic acid methylamide

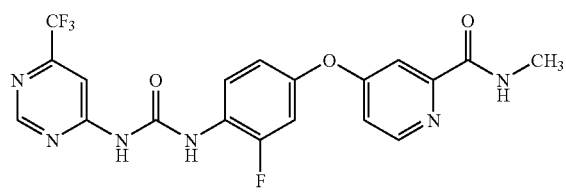 [SMILES: CNC(=O)c1cc(Oc2ccc(NC(=O)Nc3cc(C(F)(F)F)ncn3)c(F)c2)ccn1]

In a 8-mL screw-cap vial, 4-amino-6-trifluoromethylpyrimidine (170 mg, 1.04 mmol) was added to a slurry of 1,1'-carbonyldiimidazole (169 mg, 1.04 mmol) in dichloroethane (0.35 mL). The mixture was heated at 60° C. for 30 hours. 4-(4Amino-3-fluoro-phenoxy)-pyridine-2-carboxylic acid methylamide (170 mg, 1.04 mmol) was then added and the mixture was heated overnight at to 60° C. The solvent was evaporated under reduced pressure, and the solid residue was washed with methanol to give the title product as a white solid (139 mg, yield 30%). $^1$H NMR (400 MHz, DMSO-d$_6$) δ 10.6 (s, 1 H), 9.7 (s, 1 H), 9.0 (s, 1 H), 8.8 (s, 1 H), 8.5 (d, 1 H), 8.20 (m, 2 H), 7.40 (m, 2 H), 7.18 (d, 1 H), 7.10 (d, 1 H), 2.80 (s, 3 H). LC-MS m/z 451.3 [M+H]$^+$.

Example 2

4-{4-[3-(6-trifluoromethyl-pyrimidin-4-yl)-ureido]-phenoxy}-pyridine-2-carboxylic acid methylamide

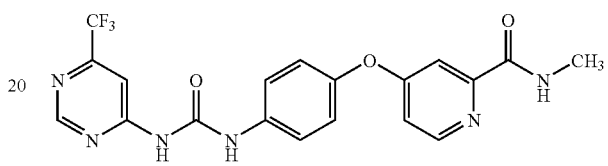

The title compound was prepared in the same manner as 4-{3-fluoro-4-[3-(6-trifluoromethylpyrimidin-4-yl)ureido]phenoxy}pyridine-2-carboxylic-acid methylamide, replacing 4-(4-amino-3-fluoro-phenoxy)pyridine-2-carboxylic acid methylamide for 4-(4-aminophenoxy)pyridine-2-carboxylic acid methylamide. LC-MS m/z 433.1 [M+H]$^+$; TLC Rf=0.8 (EtOAc).

Example 3

4-{4-[3-(6-trifluoromethylpyrimidin-4-yl)ureido]phenoxy}-2-methylpyridine

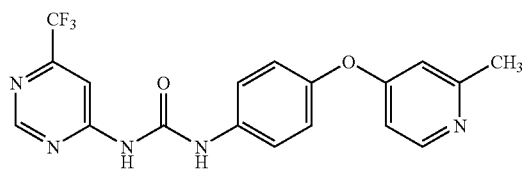 [SMILES: Cc1cc(Oc2ccc(NC(=O)Nc3cc(C(F)(F)F)ncn3)cc2)ccn1]

The title compound was prepared in the same manner as 4-{3-fluoro-4-[3-(6-trifluoromethyl-pyrimidin-4-yl)-ureido]-phenoxy}-pyridine-2-carboxylic-acid methyl-amide, replacing 4-(4-amino-3-fluorophenoxypyridine-2-carboxylic acid methylamide for 4-(2-methylpyridin-4-yloxy)phenylamine. LC-MS m/z 389.9 [M+H]$^+$; TLC Rf=0.45 (EtOAc).

Example 4

1-[2-Fluoro-4-(2-methylpyridin-4-yloxy)phenyl]-3-(6-trifluoromethylpyrimidin-4-yl)urea

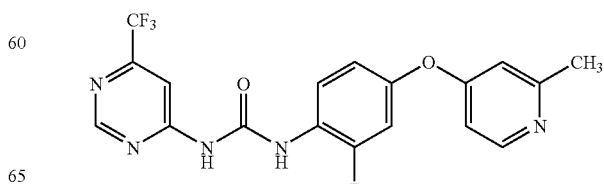

To a solution of 2-fluoro-4-(2-methylpyridin-4-yloxy)phenylamine (100 mg, 0.61 mmol) and N,N-diethylisopropylamine (0.13 mL, 0.74 mmol, 1.2 eq) in anhydrous THF (4 mL) was added triphenylphosphine (67.3 mg, 0.23 mmol, 0.37 eq) in one portion. The reaction mixture was stirred at 75° C. After 2.5 h a solution of 4-amino-6-trifluoropyrimidine (133.8 mg, 0.61 mmol, 1.0 eq) in anhydrous THF (2.5 mL) was added, and the reaction mixture was stirred at 75° C. for 16 h. The reaction mixture was then partitioned between EtOAc and saturated aqueous sodium bicarbonate solution. The organic layer was washed with water and brine, dried over sodium sulfate, filtered, and evaporated under reduced pressure. The crude oil was purified using medium pressure liquid chromatography (Biotage), eluting with 75% EtOAc/hexane. Crystallization from DCM/hexane afforded the title compound (60 mg, 24%) as a pale yellow solid. $^1$H-NMR (DMSO-d$_6$) δ 10.54 (broad s, 1H), 9.69 (broad s, 1H), 9.02 (s, 1H), 8.32 (d, J=6.0 Hz, 1H), 8.19 to 8.12 (m, 2H), 7.28 (dd, J=11.7, 2.7 Hz, 1H), 7.02 (ddd, J=9.0, 3.0, 1.2 Hz, 1H), 6.80 (d, J=2.4 Hz, 1H), 6.475 (dd, J=6.0, 2.7 Hz, 1H), 2.40 (s, 3H); LC-MS m/z 408 [M+H]$^+$, RT=2.30 min.

Example 5

1-(6-tert-Butylpyrimidin-4-yl)-3-[4-(2-cyanopyridin-4-yloxy)-2-fluorophenyl]urea

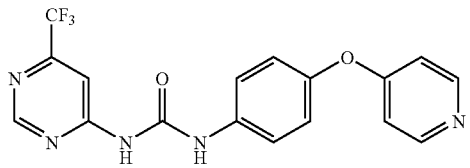 [SMILES: O=C(Nc1ccc(Oc2ccncc2)cc1)Nc1cc(C(F)(F)F)ncn1]

The title compound was prepared in the same manner described for 1-[2-fluoro-4-(2-methylpyridin-4-yloxy)phenyl]-3-(6-trifluoromethylpyrimidin-4-yl)urea, replacing 2-fluoro-4-(2-methylpyridin-4-yloxy)phenylamine for 4-(pyridin-4-yloxy)-phenylamine. $^1$H-NMR (DMSO-d$_6$) δ 10.21 (broad s, 1H), 9.68 (broad s, 1H), 8.99 (s, 1H), 8.44 to 8.43 (broad s, 2H), 8.16 (d, J=1.2 Hz, 1H), 7.60 to 7.57 (m, 2H), 7.18 to 7.14 (m, 2H), 6.88 (dd, J=4.5, 1.5 Hz, 2H); LC-MS m/z 376 [M+H]$^+$, RT=2.17 min.

Example 6

1-(6-tert-Butylpyrimidin-4-yl)-3-[4-(2-cyanopyridin-4-yloxy)-2-fluorophenyl]urea

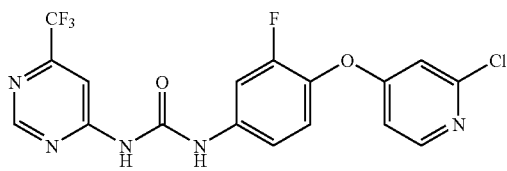 [SMILES: O=C(Nc1ccc(Oc2ccnc(Cl)c2)c(F)c1)Nc1cc(C(F)(F)F)ncn1]

The title compound was prepared in the same manner described for 1-[2-fluoro-4-(2-methylpyridin-4-yloxy)phenyl]-3-(6-trifluoromethylpyrimidin-4-yl)urea, replacing 2-fluoro-4-(2-methylpyridin-4-yloxy)phenylamine for 3-fluoro-4-(2-chloro-pyridin-4-yl-oxy)phenylamine. $^1$H-NMR (DMSO-d$_6$) δ 10.30 (broad s, 1H), 9.88 (broad s, 1H), 9.01 (s, 1H), 8.29 (d, J=6.0 Hz, 1H), 8.15 (d, J=1.2 Hz, 1H), 7.75 (dd, J=12.6, 2.7 Hz, 1H), 7.40 (t, J=8.7 Hz, 1H), 7.34 to 7.29 (m, 1H), 7.06 (d, J=2.4 Hz, 1H), 6.97 (dd, J=5.7, 2.4 Hz, 1H); LC-MS m/z 428, [M+H]$^+$, RT=3.77 min.

Example 7

4-{3-fluoro-4-[3-(6-tert-butylpyrimidin-4-yl)ureido]phenoxy}pyridine-2-carboxylic acid methylamide

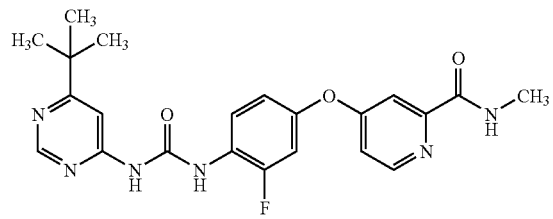 [SMILES: CNC(=O)c1cc(Oc2ccc(NC(=O)Nc3cc(C(C)(C)C)ncn3)c(F)c2)ccn1]

A solution of 6-amino-4-t-butylpyrimidine (20.0 mg; 0.13 mmol), triphosgene (14.52 mg; 0.05 mmol) and diisopropylethylamine (20.51 mg; 0.16 mmol) in THF (0.7 mL) was heated at 70° C. for 4 h. A solution of 4-(4-amino-3-fluorophenoxy)-pyridine-2-carboxylic acid methylamide (34.5 mg; 0.13 mmol) in DMF (1.5 mL) was then added and the reaction mixture was heated at 70° C. for another 8 h, then extracted between EtOAc and saturated aqueous NaHCO$_3$. The organic layer was dried and evaporated under reduced pressure to give a crude oil that was purified via HPLC to give the title compound (14 mg, 9%). $^1$H-NMR (CD$_3$OD) δ 8.73 (s, 1H), 8.48 (d, J=4.0 Hz, 1H), 8.29 (t, J=4.0 Hz, 1H), 7.57 (d, J=4.0 Hz, 1H), 7.58-7.08 (m, 3H), 7.01 (s, 1H), 2.94 (s, 3H), 1.36 (s, 9H). LC-MS m/z 439 [M+H]$^+$.

Example 8

1-(6-tert-Butylpyrimidin-4-yl)-3-[4-(2-cyanopyridin-4-yloxy)-2-fluorophenyl]urea

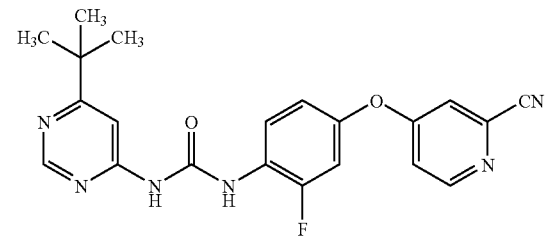 [SMILES: CC(C)(C)c1cc(NC(=O)Nc2ccc(Oc3ccnc(C#N)c3)cc2F)ncn1]

To a solution of 6-amino-4-tert-butylpyrimidine (150.0 mg; 0.99 mmol) in anhydrous 1,2-dichloroethane (1.9 mL) was added 1,1'-carbonyldi(1,2,4-triazole) (195.4 mg, 1.19 mmol, 1.2 eq), and the reaction mixture was stirred at 65° C. for 3 days. A solution of 4-(4-amino-3-fluorophenoxy)pyridine-2-carbonitrile (227.4 mg; 0.99 mmol, 1.0 eq) in anhydrous 1,2-dichloroethane (1.9 mL) was then added, and the reaction mixture was heated at 65° C. for 5 h. The reaction was diluted with EtOAc, and the organic layer was washed with water and brine, dried over sodium sulfate, and evaporated under reduced pressure to give a crude oil. Trituration from DCM afforded the title compound (211 mg, 52%) as a white solid. $^1$H-NMR (DMSO-d$_6$) δ 10.37 (broad s, 1H), 10.08 (broad s, 1H), 8.75 (d, J=1.2 Hz, 1H), 8.59 (d, J=5.4 Hz, 1H), 8.25 (t, J=9.3 Hz, 1H), 7.73 (d, J=2.7 Hz, 1H), 7.59 (s, 1H), 7.37 (dd, J=12.0, 2.7 Hz, 1H), 7.24 (dd, J=5.4, 2.4 Hz, 1H), 7.08 (ddd, J=9.0, 2.7, 1.5 Hz, 1H), 1.26 (s, 9H); LC-MS m/z 407 [M+H]$^+$, RT=3.17 min.

Example 9

4-{4-[3-(6-tert-Butylpyrimidin-4-yl)ureido]-3-fluorophenoxy}pyridine-2-carboxylic acid amide

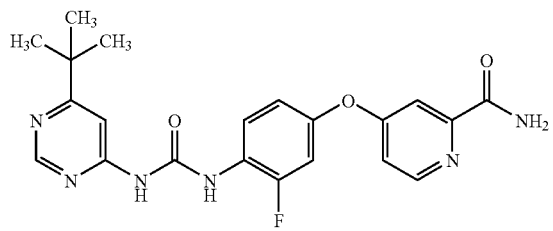 [SMILES: CC(C)(C)c1cc(NC(=O)Nc2ccc(Oc3ccnc(C(N)=O)c3)cc2F)ncn1]

A mixture of 1-(6-tert-butylpyrimidin-4-yl)-3-[4-(2-cyanopyridin-4-yloxy)-2-fluoro-phenyl]urea (141 mg, 0.35 mmol) and sodium percarbonate (with 25% H$_2$O$_2$) (218 mg, 1.4 mmol, 4.0 eq) in 2:1 v/v acetone/water (11 mL) was stirred at 60° C. for 16 h. The reaction was partitioned between ethyl acetate and water, and the aqueous layer was extracted with ethyl acetate (2×100 mL). The combined organic layers were washed with water and brine, dried over sodium sulfate, filtered, and evaporated under reduced pressure. Trituration from methanol afforded the title compound (63 mg, 43%) as a white solid. $^1$H-NMR (DMSO-d$_6$) δ 10.32 (broad s, 1H), 10.08 (broad s, 1H), 8.75 (d, J=1.2 Hz, 1H), 8.51 (d, J=5.4 Hz, 1H), 8.23 (t, J=9.3 Hz, 1H), 8.12 (broad s, 1H), 7.71 (broad s, 1H), 7.61 (d, J=1.2 Hz, 1H), 7.40 (d, J=2.4 Hz, 1H), 7.36 (dd, J=11.4, 2.4 Hz, 1H), 7.18 (dd, J=5.7, 2.7 Hz, 1H), 7.08 (ddd, J=9.0, 2.7, 1.5 Hz, 1H), 1.26 (s, 9H); LC-MS m/z 425 [M+H]$^+$, RT=3.16 min.

Example 10

4-{4-[3-(6-tert-Butylpyrimidin-4-yl)ureido]phenoxy}pyridine-2-carbothioic acid amide

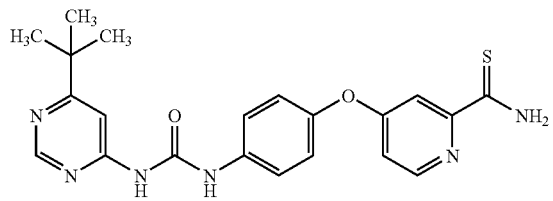 [SMILES: CC(C)(C)c1cc(NC(=O)Nc2ccc(Oc3ccnc(C(N)=S)c3)cc2)ncn1]

The title compound was prepared in the same manner as described for 1-(6-tert-butylpyrimidin-4-yl)-3-[4-(2-cyanopyridin-4-yloxy)-2-fluorophenyl]urea, replacing 4-(4-amino-3-fluorophenoxy)pyridine-2-car-bonitrile for 4-(4-aminophenoxy)pyridine-2-thioamide. $^1$H-NMR (DMSO-d$_6$) δ 10.32 (broad s, 1H), 10.20 (broad s, 1H), 10.13 (s, 1H), 9.93 (broad s, 1H), 9.72 (s, 1H), 8.74 (d, J=1.2 Hz, 1H), 8.46 (d, J=5.7 Hz, 1H), 7.95 (d, J=2.1 Hz, 1H), 7.67 (d, J=1.2 Hz, 1H), 7.64 to 7.60 (m, 2H), 7.21 to 7.17 (m, 2H), 7.12 (dd, J=5.7, 3.0 Hz, 1H), 1.26 (s, 9H); LC-MS m/z 423 [M+H]$^+$, RT=3.39 min.

Example 11

1-(6-tert-Butylpyrimidin-4-yl)-3-[4-(2-cyanopyridin-4-yloxy)-2-fluorophenyl]urea

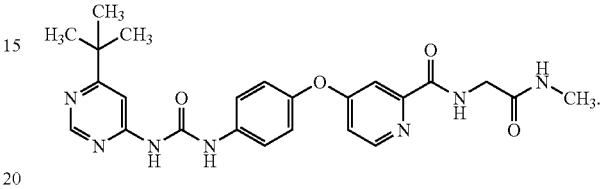

The title compound was prepared in the same manner as described for 1-(6-tert-butylpyrimidin-4-yl)-3-[4-(2-cyanopyridin-4-yloxy)-2-fluorophenyl]urea, replacing 4-(4-amino-3-fluorophenoxy)pyridine-2-carbonitrile for 4-(4-aminophenoxy)pyridine-2-carboxylic acid methylcarbamoyl-methylamide. $^1$H-NMR (DMSO-d$_6$) δ 10.10 (broad s, 1H), 9.71 (broad s, 1H), 8.87 (t, J=6.0 Hz, 1H), 8.73 (d, J=1.5 Hz, 1H), 8.52 (d, J=5.4 Hz, 1H), 7.85 to 7.80 (m, 1H), 7.67 (d, J=1.2 Hz, 1H), 7.63 to 7.60 (m, 2H), 7.35 (d, J=2.4 Hz, 1H), 7.19 to 7.15 (m, 3H), 3.82 (d, J=6.0 Hz, 2H), 2.55 (d, J=4.2 Hz, 3H), 1.25 (s, 9H); LC-MS m/z 478 [M+H]$^+$, RT=2.47 min.

Example 12

4-{3-fluoro-4-[3-(6-methoxypyrimidin-4-yl)ureido]phenoxy}pyridine-2-carboxylic acid methylamide

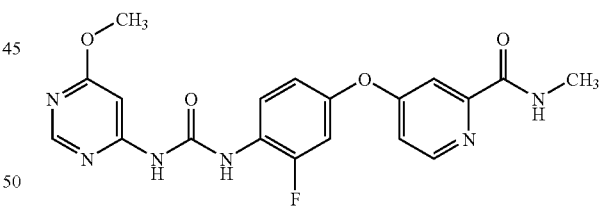

A solution of 6-amino-4-methoxypyrimidine (50.0 mg; 0.39 mmol), triphosgene (43.0 mg; 0.14 mmol) and diisopropylethylamine (60.7 mg; 0.47 mmol) in THF (2.0 mL) was heated at 70° C. for 4 h. A solution of 4-(4-amino-3-fluorophenoxy)-pyridine-2-carboxylic acid methylamide (102.3 mg; 0.39 mmol) in DMF (1.0 mL) was then added, and the reaction mixture was heated at 70° C. for another 8 h, then extracted between EtOAc and saturated aqueous NaHCO$_3$. The organic layer was dried and evaporated to give a crude oil that was purified via HPLC to give the title compound (14 mg, 9%). $^1$H-NMR (CD$_3$OD) δ 8.36 (s, 1H), 8.35 (s, 1H), 8.14 (t, J=8.8 Hz, 1H), 7.46 (d, J=2.4 Hz, 1H), 7.00-6.86 (m, 3H), 6.60 (s, 1H), 3.86 (s, 3H), 2.83 (s, 3H); LC-MS m/z 413 [M+H]$^+$.

Example 13

4-{4-[3-(6-Phenylpyrimidin-4-yl)ureido]phenoxy}pyridine-2-carbothioic acid amide

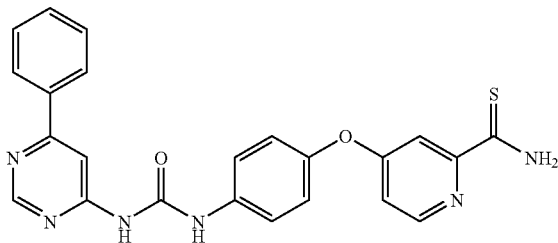 [SMILES: NC(=S)c1cc(Oc2ccc(NC(=O)Nc3cc(-c4ccccc4)ncn3)cc2)ccn1]

The title compound was prepared in the same manner as described for 4-{-4-[3-(6-tert-butylpyrimidin-4-yl)ureido]phenoxy}pyridine-2-carbothioic acid amide, replacing 6-amino-4-tert-butylpyrimidine for 6-amino-4-phenylpyrimidine. $^1$H-NMR (DMSO-$d_6$) δ 10.18 (broad s, 1H), 10.04 (broad s, 1H), 9.91 (broad s, 1H), 9.85 (broad s, 1H), 8.78 (d, J=1.2 Hz, 1H), 8.45 (d, J=5.7 Hz, 1H), 8.15 (s, 1H), 8.06 to 8.02 (m, 2H), 7.94 (d, J=2.7 Hz, 1H), 7.64 (d, J=8.7 Hz, 2H), 7.54 to 7.52 (m, 3H), 7.20 (d, J=8.7 Hz, 2H), 7.12 (dd, J=5.7, 3.0 Hz, 1H); LC-MS m/z 443 [M+H]$^+$, RT=3.19 min.

Example 14 c-raf (raf-1) Biochemical Assay

The c-raf biochemical assay was performed with a c-raf enzyme that was activated (phosphorylated) by Lck kinase. Lck-activated c-raf (Lck/c-raf) was produced in Sf9 insect cells by co-infecting cells with baculoviruses expressing, under the control of the polyhedrin promoter, GST-c-raf (from amino acid 302 to amino acid 648) and Lck (full-length). Both baculoviruses were used at the multiplicity of infection of 2.5 and the cells were harvested 48 h post infection.

MEK-1 protein was produced in Sf9 insect cells by infecting cells with the baculovirus expressing GST-MEK-1 (full-length) fusion protein at the multiplicity of infection of 5 and harvesting the cells 48 hours post infection. Similar purification procedure was used for GST-c-raf 302-648 and GST-MEK-1.

Transfected cells were suspended at 100 mg of wet cell biomass per mL in a buffer containing 10 mM sodium phosphate, 140 mM sodium chloride pH 7.3, 0.5% Triton X-100 and the protease inhibitor cocktail. The cells were disrupted with Polytron homogenizer and centrifuged 30,000 g for 30 minutes. The 30,000 g supernatant was applied onto GSH-Sepharose. The resin was washed with a buffer containing 50 mM Tris, pH 8.0, 150 mM NaCl and 0.01% Triton X-100. The GST-tagged proteins were eluted with a solution containing 100 mM Glutathione, 50 mM Tris, pH 8.0, 150 mM NaCl and 0.01% Triton X-100. The purified proteins were dialyzed into a buffer containing 20 mM Tris, pH 7.5, 150 mM NaCl and 20% Glycerol.

Test compounds were serially diluted in DMSO using three-fold dilutions to stock concentrations ranging typically from 50 μM to 20 nM (final concentrations in the assay range from 1 μM to 0.4 nM). The c-Raf biochemical assay was performed as a radioactive filtermat assay in 96-well Costar polypropylene plates (costar 3365). The plates were loaded with 75 μL solution containing 50 mM HEPES pH 7.5, 70 mM NaCl, 80 ng of Lck/c-raf and 1 μg MEK-1. Subsequently, 2 μL of the serially diluted individual compounds were added to the reaction, prior to the addition of ATP. The reaction was initiated with 25 μL ATP solution containing 5 μM ATP and 0.3 μCi [33P]-ATP. The plates were sealed and incubated at 32° C. for 1 h. The reaction was quenched with the addition of 50 μL of 4% Phosphoric Acid and harvested onto P30 filtermats (PerkinElmer) using a Wallac Tomtec Harvester. Filtermats were washed with 1% Phosphoric Acid first and deionized H$_2$O second. The filters were dried in a microwave, soaked in scintillation fluid and read in a Wallac 1205 Betaplate Counter (Wallac Inc., Atlanta, Ga., U.S.A.). The results were expressed as percent inhibition.

% Inhibition=[100−($T_{ib}$($T_i$)]×100 where
$T_{ib}$=(counts per minute with inhibitor)−(background)
$T_i$=(counts per minute without inhibitor)−(background)

Example 15 flk-1 (Murine VEGFR-2) Biochemical Assay

This assay was performed in 96-well opaque plates (Costar 3915) in the TR-FRET format. Reaction conditions are as follows: 10 μM ATP, 25 nM poly GT-biotin, 2 nM Eu-labelled phospho-Tyr Ab, 10 nM APC, 7 nM flk-1 (kinase domain), 1% DMSO, 50 mM HEPES pH 7.5, 10 mM MgCl$_2$, 0.1 mM EDTA, 0.015% BRIJ, 0.1 mg/mL BSA, 0.1% mercapto-ethanol). Reaction is initiated upon addition Of enzyme. Final reaction volume in each well is 100 μL. Plates are read at both 615 and 665 nM on a Perkin Elmer Victor V Multilabel counter at about 1.5-2.0 hours after reaction initiation. Signal is calculated as a ratio: (665 nm/615 nm)*10000 for each well.

For IC$_{50}$ generation against flk-1 kinase, test compounds were added prior to the enzyme initiation. A 50-fold stock plate was made with compounds serially diluted 1:3 in a 50% DMSO/50% dH2O solution. A 2 μL addition of the stock to the assay gave final compound concentrations ranging from 10 μM−4.56 nM in 1% DMSO. The data were expressed as percent inhibition: % inhibition=100−((Signal with inhibitor-background)/(Signal without inhibitor-background))*100.

Compounds of examples 1-13 showed significant inhibition (IC$_{50}$<10 μM) in either or both the c-raf and flk-1 biochemical assays.

What is claimed is:

1. A compound of formula (I), a salt thereof, an oxidized derivative thereof, wherein one or more of the nitrogens are substituted with a hydroxy group, or a diastereoisomeric form thereof, either as an isolated stereoisomer or in a mixture of stereoisomers

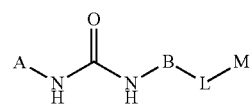

I wherein
A is pyrimidine,
optionally substituted with 1 to 3 substituents which are independently R$^1$, OR$^1$, S(O)$_p$R$^1$, C(O)R$^1$, C(O)OR$^1$, C(O)NR$^1$R$^2$, halogen, hydroxy, amino, cyano, or nitro;
B is phenyl, naphthyl, or pyridyl, optionally substituted with 1 to 4 substituents which are independently C$_1$-C$_5$ linear or branched alkyl, C$_1$-C$_5$ linear or branched haloalkyl, $C_1$-$C_3$ alkoxy, hydroxy, amino, $C_1$-$C_3$ alkylamino, $C_1$-$C_6$ dialkylamino, halogen, cyano, or nitro;

L is a bridging group which is:
(a) —$(CH_2)_m$—O—$(CH_2)_l$—,
(b) —$(CH_2)_m$—$(CH_2)_l$—,
(c) —$(CH_2)_m$—C(O)—$(CH_2)_l$—,
(d) —$(CH_2)_m$—$NR^3$—$(CH_2)_l$—,
(e) —$(CH_2)_m$—$NR^3C(O)$—$(CH_2)_l$—,
(f) —$(CH_2)_m$—S—$(CH_2)_l$—, or
(g) —$(CH_2)_mC(O)NR^3$—$(CH_2)_l$—, where the integers m and l are independently selected from 0-4 and for —$(CH_2)_m$—$(CH_2)_l$— m and l cannot both be 0;

M is a pyridine or pyrimidine ring, optionally substituted with 1-3 substituents which are independently selected from:
(1) $C_1$-$C_5$ linear or branched alkyl;
(2) $C_1$-$C_5$ linear or branched haloalkyl;
(3) $C_1$-$C_3$ alkoxy;
(4) hydroxy;
(5) amino;
(6) $C_1$-$C_3$ alkylamino;
(7) $C_1$-$C_6$ dialkylamino;
(8) halogen;
(9) nitro;
(10) C(O) $NR^4R^5$;
(11) C(O)$OR^4$;
(12) C(O)$R^4$;
(13) CN;
(14) C(S)$NR^4R^5$;
(15a) C(O)$NR^7$—$NR^4R^5$;
(15b) C(O)$NR^7$—$R^4$—C(O)$NR^4R^5$;
(16) tetrazolyl;
(17) imidazolyl;
(18) imidazoline-2-yl;
(19) 1,3,4-oxadiazoline-2-yl;
(20) 1,3-thiazoline-2-yl;
(21) 5-thioxo-4,5-dihydro-1,3,4-thiazoline-2-yl;
(22) 5-oxo-4,5-dihydro-1,3,4-oxadiazoline-2-yl; or
(23) a group of the formula

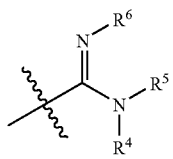

each of $R^1$, $R^2$, $R^3$, $R^4$ and $R^5$ is independently
(a) hydrogen,
(b) $C_1$-$C_5$ linear, branched, or cyclic alkyl,
(c) up to per-halo substituted $C_1$-$C_5$ linear or branched alkyl, or
(d) —$(CH_2)_q$—X.
where the substituent X is a 5 or 6 membered heterocyclic ring, containing at least one atom selected from oxygen, nitrogen and sulfur, which is saturated, partially saturated, or aromatic, or a 8-10 membered bicyclic heteroaryl having 1-4 heteroatoms selected from the group consisting of O, N and S;
$R^2$, $R^3$, $R^4$ and $R^5$ may, independently, additionally include phenyl or $C_1$-$C_3$ phenyl-alkyl;
$R^4$ and $R^5$ may optionally be taken together to form a 5 or 6 membered aliphatic ring, which may be interrupted by an atom selected from N, O or S which is optionally substituted with 1-3 substituents which are independently $C_1$-$C_5$ linear or branched alkyl, up to perhalo substituted $C_1$-$C_5$ linear or branched alkyl, $C_1$-$C_3$ alkoxy, hydroxy, oxo, carboxy, amino, $C_1$-$C_3$ alkylamino, $C_1$-$C_6$ dialkylamino, halogen, cyano, or nitro;

$R^6$ is independently:
(a) hydrogen,
(b) $C_1$-$C_5$ linear, branched, or cyclic alkyl,
(c) cyano,
(d) nitro,
(e) up to per-halo substituted $C_1$-$C_5$ linear or branched alkyl, or
(f) —C(O)$R^7$, where $R^7$ is $C_1$-$C_5$ linear, branched, or cyclic alkyl;

$R^7$ is hydrogen, or $C_1$-$C_5$ linear, branched, or cyclic alkyl; the variable q is an integer 1, 2, 3, or 4 and the variable p is an integer 0, 1, or 2.

2. A compound of claim 1 wherein B is phenyl, optionally substituted with 1-4 substituents which are independently $C_1$-$C_5$ linear or branched alkyl, $C_1$-$C_5$ linear or branched haloalkyl, $C_1$-$C_3$ alkoxy, hydroxy, amino, $C_1$-$C_3$ alkylamino, $C_1$-$C_6$ dialkylamino, halogen, cyano, or nitro.

3. A compound of claim 1 or 2 where L is —O— or —S—.

4. A compound of claim 1, where M is pyridine, optionally substituted with 1-3 substituents which are independently selected from the groups
(1) $C_1$-$C_5$ linear or branched alkyl;
(2) $C_1$-$C_5$ linear or branched haloalkyl;
(3) $C_1$-$C_3$ alkoxy;
(4) hydroxy;
(5) amino;
(6) $C_1$-$C_3$ alkylamino;
(7) $C_1$-$C_6$ dialkylamino;
(8) halogen;
(9) nitro;
(10) C(O) $NR^4R^5$;
(11) C(O)O $R^4$;
(12) C(O) $R^4$;
(13) CN,
(15a) C(O)$NR^7$—$NR^4R^5$; or
(15b) C(O)$NR^7$—$R^4$—C(O)$NR^4R^5$.

5. A compound of claim 1 where $R^6$ is independently:
(a) hydrogen,
(b) $C_1$-$C_5$ linear, branched, or cyclic alkyl, or
(c) cyano or
(d) nitro.

6. A compound of claim 1 where $R^6$ is independently:
(a) hydrogen,
(b) $C_1$-$C_5$ linear, branched, or cyclic alkyl, or
(c) cyano.

7. A compound of claim 1 of formula (III), a salt thereof, an oxidized derivative thereof, wherein one or more of the nitrogens are substituted with a hydroxy group, or a diastereoisomeric form thereof, either as an isolated stereoisomer or in a mixture of stereoisomers, (III)

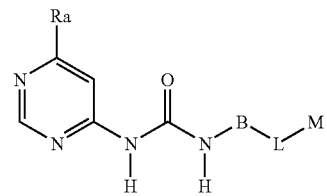

wherein

Ra is $R^1$, $OR^1$ or cyano;

and B, L and M are as defined in claim 1.

8. A compound of claim 1 of formula (IV), a salt thereof, an oxidized derivative thereof, wherein one or more of the nitrogens are substituted with a hydroxy group, or a diastereoisomeric form thereof, either as an isolated stereoisomer or in a mixture of stereoisomers,

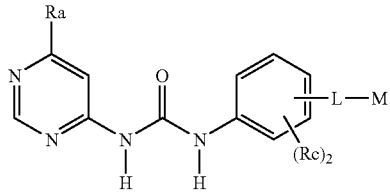

(IV)

wherein

Ra is $R^1$, $OR^1$ or cyano;

each Rc is independently hydrogen, halogen, $C_1$-$C_3$ linear or branched alkyl, $C_1$-$C_3$ linear or branched haloalkyl, $C_1$-$C_3$ alkoxy or hydroxy;

and

L and M are as defined in claim 1.

9. A compound of claim 1 of formula (V), a salt thereof, an oxidized derivative thereof, wherein one or more of the nitrogens are substituted with a hydroxy group, or a diastereoisomeric form thereof, either as an isolated stereoisomer or in a mixture of stereoisomers,

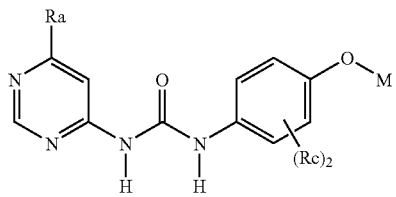

(V)

wherein

Ra is $R^1$, $OR^1$ or cyano;

each Rc is independently hydrogen, halogen, $C_1$-$C_3$ linear or branched alkyl, $C_1$-$C_3$ linear or branched haloalkyl, $C_1$-$C_3$ alkoxy or hydroxy;

and M is as defined in claim 1.

10. A compound as in claim 8 or 9 wherein M is pyridine.

11. A compound as in claim 8 or 9 where in M is pyridine substituted by $C(O)$ $NR^4R^5$ or CN.

12. A compound as in claim 8 or 9 where in M is pyridine substituted by $C(O)$ $NR^4R^5$.

13. A compound as in claim 8 or 9 where in M is pyridine substituted by $C(O)$ $NHCH_3$ or $C(O)NH_2$.

14. A compound of formula (II), a salt thereof, an oxidized derivative thereof, wherein one or more of the nitrogens are substituted with a hydroxy group, or a diastereoisomeric form thereof, either as an isolated stereoisomer or mixture of stereoisomers,

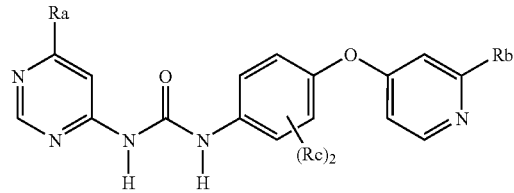

(II)

wherein

Ra is $R^1$, $OR^1$ or cyano each Rc is independently hydrogen, halogen, $C_1$-$C_3$ linear or branched alkyl, $C_1$-$C_3$ linear or branched haloalkyl, $C_1$-$C_3$ alkoxy or hydroxy;

Rb is (1) $C_1$-$C_5$ linear or branched alkyl;
(2) $C_1$-$C_5$ linear or branched haloalkyl;
(3) $C_1$-$C_3$ alkoxy;
(4) hydroxy;
(5) amino;
(6) $C_1$-$C_3$ alkylamino;
(7) $C_1$-$C_6$ dialkylamino;
(8) halogen;
(9) nitro;
(10) $C(O)$ $NR^4R^5$;
(11) $C(O)OR4$;
(12) $C(O)R^4$;
(13) CN;
(14) $C(S)NR^4R^5$;
(15) $C(O)NR^7$—$R^4C(O)N$ $R^4R^5$; or
(16) hydrogen;

$R^1$ is hydrogen or $C_1$-$C_5$ linear, branched, or cyclic alkyl, each of $R^4$ and $R^5$ is independently (a) hydrogen,
(b) $C_1$-$C_5$ linear, branched, or cyclic alkyl or
(c) phenyl, and $R^7$ is hydrogen, or $C_1$-$C_5$ linear, branched, or cyclic alkyl.

15. A compound of claim 14 wherein Rb is
$C_1$-$C_5$ linear or branched alkyl;
$C_1$-$C_3$ alkoxy;
halogen;
$C(O)$ $NR^4R^5$;
CN;
$C(S)NR^4R^5$ or $C(O)NR^7$—$R^4C(O)N$ $R^4R^5$.

16. A compound of claim 14 wherein Rb is $C_1$-$C_5$ linear or branched alkyl; halogen; $C(O)$ $NR^4R^5$ or CN.

17. A compound of claim 14, 15 or 16 wherein Rc is independently hydrogen or fluorine.

18. A compound of claim 14 wherein Rb is $C(O)$ $NR^4R^5$ or CN.

19. A compound of claim 14 wherein Rb is $C(O)$ $NR^4R^5$.

20. A compound of claim 14 wherein Rb is $C(O)$ $NHCH_3$ or $C(O)$ $NH_2$.

21. A compound of claim 1 which is:
4-{3-fluoro-4-[3-(6-trifluoromethylpyrimidin-4-yl)ureido]phenoxy}pyridine-2-carboxylic acid methylamide,
4-{4-[3-(6-trifluoromethyl-pyrimidin-4-yl)-ureido]-phenoxy}-pyridine-2-carboxylic acid methylamide,
4-{4-[3-(6-trifluoromethylpyrimidin-4-yl)ureido]phenoxy}-2-methylpyridine,
1-[2-Fluoro-4-(2-methylpyridin-4-yloxy)phenyl]-3-(6-trifluoromethylpyrimid-in-4-yl)urea,
1-(6-tert-Butylpyrimidin-4-yl)-3-[4-(2-cyanopyridin-4-yloxy)-2-fluoropheny-l]urea, 4-{3-fluoro-4-[3-(6-tert-butylpyrimidin-4-yl)ureido]
phenoxy}pyridine-2-carboxylic acid methylamide, 4-{4-[3-(6-tert-Butylpyrimidin-4-yl)ureido]-3-
fluorophenoxy}pyridine-2-carboxylic acid amide, 4-{4-[3-(6-tert-Butylpyrimidin-4-yl)ureido]
phenoxy}pyridine-2-carbothioic acid amide, 4-{3-fluoro-4-[3-(6-methoxypyrimidin-4-yl)ureido]
phenoxy}pyridine-2-carboxylic acid methylamide, or 4-{4-[3-(6-Phenylpyrimidin-4-yl)ureido]
phenoxy}pyridine-2-carbothioic acid amide.

\* \* \* \* \*

UNITED STATES PATENT AND TRADEMARK OFFICE
CERTIFICATE OF CORRECTION

PATENT NO.        : 8,580,798 B2                                    Page 1 of 1
APPLICATION NO.   : 12/158524
DATED             : November 12, 2013
INVENTOR(S)       : Smith et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1205 days.

Signed and Sealed this
Twenty-second Day of September, 2015

Michelle K. Lee
*Director of the United States Patent and Trademark Office*